United States Patent [19]

Sato et al.

[11] Patent Number: 5,528,371
[45] Date of Patent: Jun. 18, 1996

[54] MEASUREMENT APPARATUS FOR MEASURING DIMENSIONS OF SEMICONDUCTOR DEVICE AND METHOD OF MEASURING THE SAME

[75] Inventors: Hajime Sato; Yoshikazu Sakaue, both of Itami, Japan

[73] Assignee: Mitsubishi Denki Kabushiki Kaisha, Tokyo, Japan

[21] Appl. No.: 361,224

[22] Filed: Dec. 21, 1994

[30] Foreign Application Priority Data

Dec. 21, 1993 [JP] Japan .................................... 5-322702

[51] Int. Cl.⁶ .......................... G01B 11/00; G01N 21/88
[52] U.S. Cl. .................. 356/372; 356/383; 356/394; 356/237; 348/126; 348/130; 348/131; 382/146; 382/149
[58] Field of Search ..................... 356/372, 375, 356/383, 394, 237, 371; 382/145, 146, 149; 348/126, 129, 130, 131

[56] References Cited

FOREIGN PATENT DOCUMENTS 3219655  9/1991  Japan .

Primary Examiner—F. L. Evans
Attorney, Agent, or Firm—Leydig, Voit & Mayer

[57] ABSTRACT

A measurement apparatus includes two mirrors reflecting light rays obtained when a group of leads arranged on one lateral surface of a semiconductor device and a light-shielding band pattern are illuminated in two different directions. The measurement apparatus thus inputs the light rays into a single imaging device without moving the semiconductor device and the transparent mounting plate so that the distance traveled by one light ray from an illumination unit to the imaging device is equal to the distance traveled by the other light ray through the mirror to a second imaging device. Thus, an inexpensive measurement apparatus automatically measures the dimensions of a semiconductor device at high speed using an automatic feeding function and to produces highly accurate measurements.

13 Claims, 29 Drawing Sheets

| 3 | 2 | 4 | 2 | 2 | 4 | 4 | 3 |
|---|---|---|---|---|---|---|---|
| 3 | 6 | 3 | 5 | 3 | 5 | 2 | 5 |
| 6 | 2 | 2 | 10 | 16 | 18 | 22 | 21 |
| 2 | 3 | 4 | 15 | 30 | 35 | 40 | 39 |
| 4 | 5 | 3 | 19 | 38 | 61 | 63 | 62 |
| 5 | 6 | 2 | 21 | 45 | 63 | 80 | 81 |
| 1 | 6 | 3 | 19 | 42 | 65 | 62 | 84 |
| 2 | 4 | 3 | 20 | 40 | 60 | 80 | 85 |

| 0 | 0 | 0 | 0 | 0 | 0 | 0 |
|---|---|---|---|---|---|---|
| 0 | 0 | 0 | 0 | 0 | 0 | 0 |
| 0 | 0 | 0 | 0 | 0 | 0 | 0 |
| 0 | 0 | 11 | 26 | 0 | 0 | 0 |
| 0 | 0 | 16 | 35 | 58 | 0 | 0 |
| 0 | 0 | 19 | 43 | 61 | 78 | 0 |
| 0 | 0 | 16 | 39 | 62 | 79 | 0 |
| 0 | 0 | 17 | 37 | 57 | 77 | 0 |

89

PREDETERMINED VALUE 82a=10

| 0 | 0 | 0 | 0 | 0 | 0 | 0 | 0 |
|---|---|---|---|---|---|---|---|
| 0 | 0 | 0 | 0 | 0 | 0 | 0 | 0 |
| 0 | 0 | 0 | 0 | 13 | 13 | 20 | 16 |
| 0 | 0 | 0 | 0 | 27 | 30 | 38 | 34 |
| 0 | 0 | 0 | 0 | 0 | 56 | 61 | 57 |
| 0 | 0 | 0 | 0 | 0 | 0 | 78 | 76 |
| 0 | 0 | 0 | 0 | 0 | 0 | 0 | 0 |

89

PREDETERMINED VALUE 82a=10

FIG. 15

| 0 | 0 | 0 | 0 | 0 | 0 | 0 |
|---|---|---|---|---|---|---|
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 0 | 0 | 0 | 0 | 0 |
| 0 | 0 | 1 | 0 | 0 | 0 | 0 |
| 0 | 0 | 0.83 | 0 | 0 | 0 | 0 |
| 0 | 0 | 0 | 1 | 0 | 0 | 0 |
| 0 | 0 | 0 | 0.02 | 0 | 0 | 0 |
| 0 | 0 | 0 | 1 | 0 | 0 | 0 |
| 0 | 0 | 0 | 0.08 | 0 | 0 | 0 |

EDGE POSITION REFERENCE VALUE 90 = 65

FIG. 16

| 0 | 0 | 0 | 0 | 0 | 0 | 0 | 0 |
|---|---|---|---|---|---|---|---|
| 0 | 0 | 0 | 0 | 0 | 0 | 0 | 0 |
| 0 | 0 | 0 | 0 | 0 | 0 | 0 | 0 |
| 0 | 0 | 0 | 0 | 0 | 0 | 0 | 0 |
| 0 | 0 | 0 | 0 | 0 | 0 | 0 | 0 |
| 0 | 0 | 0 | 0 | 0 | 0 | 0 | 0 |
| 0 | 0 | 0 | 0 | 0 | 0 | 1 | 1 |
| 0 | 0 | 0 | 0 | 0 | 0 | 0.04 | 0.17 |
| 0 | 0 | 0 | 0 | 0 | 0 | 0 | 0 |
| 0 | 0 | 0 | 0 | 0 | 0 | 0 | 0 |
| 0 | 0 | 0 | 0 | 0 | 0 | 0 | 0 |
| 0 | 0 | 0 | 0 | 0 | 0 | 0 | 0 |
| 0 | 0 | 0 | 0 | 0 | 0 | 0 | 0 |
| 0 | 0 | 0 | 0 | 0 | 0 | 0 | 0 |

EDGE POSITION REFERENCE VALUE 90 = 65

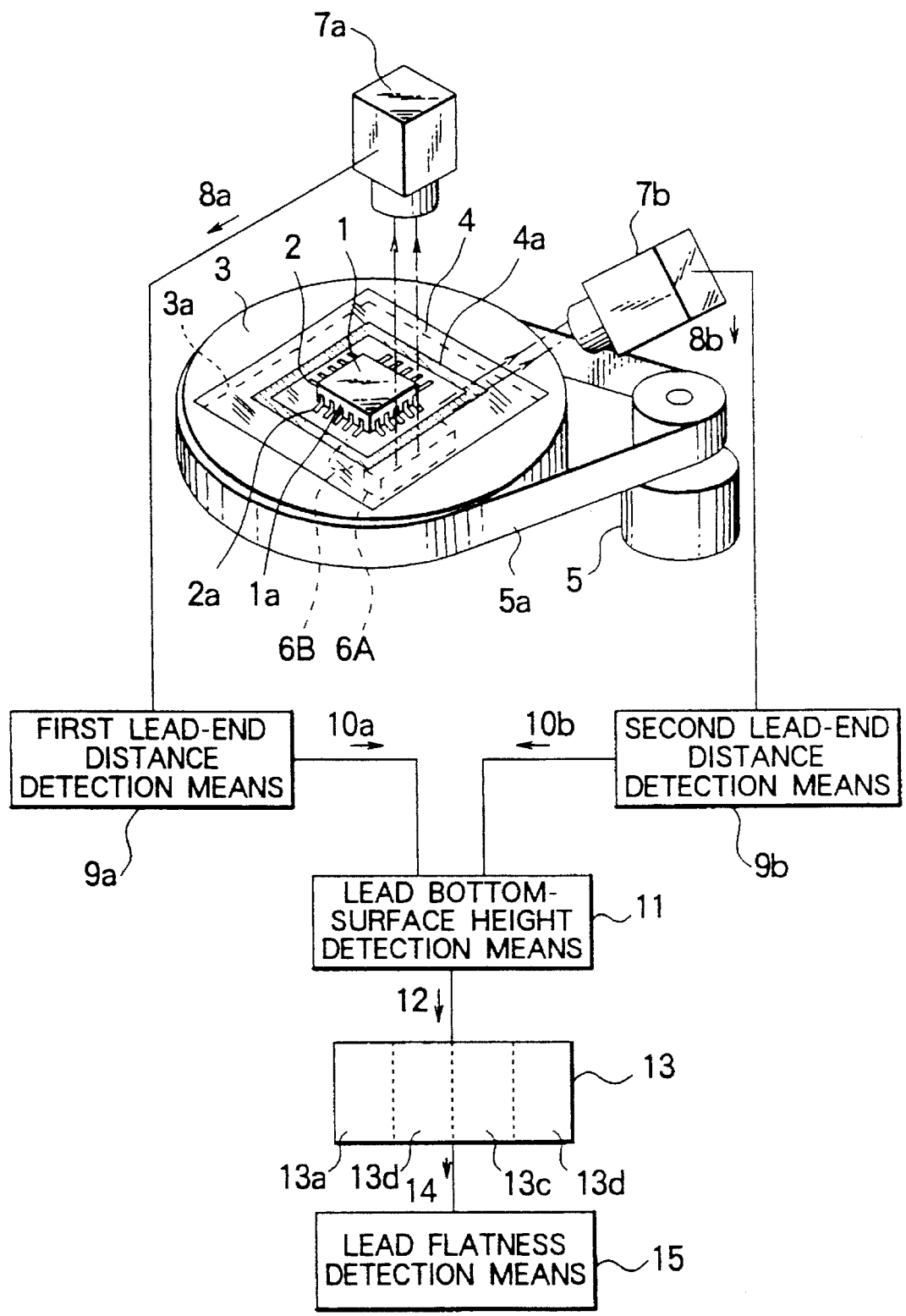

5,528,371

MEASUREMENT APPARATUS FOR MEASURING DIMENSIONS OF SEMICONDUCTOR DEVICE AND METHOD OF MEASURING THE SAME

BACKGROUND OF THE INVENTION

1. Field of the Invention

The present invention relates to a measurement apparatus and a measurement method. More particularly, the invention relates to a measurement apparatus for measuring the dimensions of the outer configuration of a surface mounted-type semiconductor device and a method of measuring the same.

2. Description of the Related Art

FIG. 33 is a schematic view illustrative of the construction of a lead flatness measurement apparatus for a conventional semiconductor device by way of example. FIG. 33 shows a semiconductor device 1, a package 1a for the semiconductor device 1, leads 2 of the semiconductor device 1, end surfaces 2a of the leads 2, a mounting base 3 for having the semiconductor device 1 mounted thereon, a pit 3a of the mounting base 3, a transparent mounting plate 4 fit into the mounting base 3 so as to have the semiconductor device 1 mounted thereon, a light-shielding band pattern 4a on the transparent mounting plate 4, a drive electric motor 5 for rotating the mounting base 3, a belt 5a connecting the mounting base 3 and the electric motor 5, and first and second illumination units 6A and 6B for illuminating the semiconductor device 1 from below through the transparent mounting plate 4.

FIG. 33 further shows: a first imaging device 7a for forming an image of the semiconductor device 1 and the light-shielding band pattern 4a from respective angles of elevation; a second imaging device 7b for forming an image of the semiconductor device 1 and the light-shielding band pattern 4b from different angles of elevation from those of the first imaging device 7a; first and second image information items 8a and 8b which are output from the first and second imaging devices 7a and 7b, respectively; first and second lead-end distance detection means 9a and 9b for receiving the first and second image information items 8a and 8b, respectively; first and second distance information items 10a and 10b which are output from the first and second lead-end distance detection means 9a and 9b, respectively; lead height detection means 11 for detecting the height from the bottom surface of each of the leads so as to receive the first and second distance information items 10a and 10b; lead height information 12 which is output from the lead height detection means 11; a storage device 13 including divided components 13a–13d for storing the lead height information 12 therein; lead height information 14 which is output from the storage device 13; and lead flatness detection means 15 for receiving the lead height information 14.

A description will now be given of the operation of the conventional lead flatness measurement apparatus constructed as described above. The surface mounted-type semiconductor device 1 is constructed such that a plurality of leads 2 projects downward from each lateral surface of the package 1a formed of a sealing resin, the forward end of each lead 2 being horizontally bent outward. The mounting base 3 is rotatably supported by supporting means (not shown). The light-shielding band pattern 4a is formed on the top surface of the transparent mounting plate 4 which is fit into the pit 3a of the mounting base 3 so as to opposedly face, across a predetermined distance, the end surfaces 2a of the leads 2 on each lateral surface of the semiconductor device 1.

The drive electric motor 5 gradually rotates the mounting base 3 by 90° via the belt 5a. Further, the first illumination unit 6A is placed to apply light downward that is reflected upward from the end surfaces 2a of the leads 2 arranged on one lateral surface of the semiconductor device 1, while the second illumination unit 6B is placed to apply light to the end surfaces 2a of the leads 2 in an obliquely upward direction. The first imaging device 7a is placed above the first illumination unit 6A so as to forming an image of the end surfaces 2a of the leads 2 and to output the image information item 8a to the first lead-end distance detection means 9a. On the other hand, the second imaging device 7b is placed in an obliquely upward direction of the second illumination unit 6B so as to forming an image of the end surfaces 2a of the leads 2 and to output the image information item 8b to the second lead-end distance detection means 9b.

The first lead-end distance detection means 9a detects the distance between the end surface 2a of the lead 2 and the light-shielding band pattern 4a according to the image information item 8a. The second lead-end distance detection means 9b detects the distance between the end surface 2a of the lead 2 and the light-shielding band pattern 4a according to the image information item 8b. The first and second distance information items 10a and 10b are input into the lead height detection means 11 from the first and second lead-end distance detection means 9a and 9b, respectively, so that the lead height detection means 11 can detect the height from the bottom surface of the lead 2 and the transparent mounting plate 4. The lead height information 12 is input into the storage device 13 from the lead height detection means 11. More specifically, the height information items for respective groups of the leads 2 on the respective lateral surfaces of the semiconductor device 1 are respectively input into the divided components 13a–13d of the storage device 13. The lead flatness detection means 15 receives the height information items 12 concerning the respective groups of the leads 2, which information items 12 are output from the storage means 13, so as to detect the maximum height among the height information items 12 as the lead flatness.

The lead flatness measurement apparatus described above presents the following problems. The mounting base 3 is rotated at low speed in order to avoid the displacement of the semiconductor device 1. It thus requires a long time to measure the flatness of all the leads of the semiconductor device 1. Further, if an imaging device is arranged on each lateral surface having the leads 2 of the semiconductor 1 projecting therefrom, it intervenes with the automatic feeding of the semiconductor device 1. Since the leads 2 are tilted, the first and second imaging devices 7a and 7b unfavorably forming images of the end surfaces 2a of the different leads 2, thereby lowering measurement accuracy. Moreover, since the measurement apparatus does not recognize the bottom surface of the package 1a of the semiconductor device 1, it is unable to measure the stand-off characteristics and the lead length of the semiconductor device 1. Additionally, it is impossible to carry out measurements if foreign matter adheres to the transparent mounting plate 4, or if the mounting plate 4 is scratched.

SUMMARY OF THE INVENTION

Accordingly, in order to overcome the above drawbacks, an object of the present invention is to provide an inexpensive measurement apparatus which automatically measures the dimensions of a semiconductor device at high speed using automatic feeding means and which enables measurements with high accuracy, and also to provide a method of measuring the dimensions of a semiconductor device.

In order to achieve the above objects, according to a first aspect of the present invention, there is provided a measurement apparatus for measuring the dimensions of a semiconductor device, comprising: a transparent mounting plate having a surface mounted-type semiconductor device mounted thereon and having a light-shielding band pattern formed thereon; an illumination unit placed under the transparent mounting plate; first and second imaging devices for forming images and producing first and second optical information items, respectively, which are output from the illumination unit and which are formed by applying light to a lateral surface of the semiconductor device and the light-shielding band pattern at large and small angles of elevation along the axis of leads projecting from the lateral surface; first and second optical information reflecting means for reflecting the first and second optical information items, respectively, and allowing them to impinge on the first and second imaging devices, respectively; and optical reflecting means arranged between the first optical information reflecting means and the first imaging device and also arranged between the second optical information reflecting means and the second imaging device so that a distance of the first optical information from the illumination unit to the first imaging device is equal to a distance of the second optical information from the illumination unit to the second imaging device.

According to a second aspect of the present invention, there is provided a method of measuring the dimensions of a semiconductor device, comprising the steps of: applying light by illumination units in two different directions to a group of leads arranged on one lateral surface of a semiconductor device and to a light-shielding band pattern on a transparent mounting plate for having the semiconductor device mounted thereon; forming images and producing two optical information items through reflecting means by a single imaging device, the optical information items being obtained by applying light to the semiconductor device and the light-shielding band pattern; storing respective image information items obtained by the imaging device; detecting a position of a forward end of each of the leads arranged on one lateral surface of the semiconductor device and a position of the light-shielding band pattern corresponding to each of the leads, the detection being performed by position detection means for each of the optical information items having different directions; measuring a distance from the forward end of each of the leads to the light-shielding band pattern corresponding to each of the leads, the measurement being performed by distance measurement means for each of the optical information items having different directions; measuring the flatness of each of the leads by flatness measurement means from distance information items obtained for the two optical information items having different directions and from known angles of elevation of the two optical information items; and sequentially measuring the flatness of the leads according to the image information items indicative of the respective lateral surfaces each having the leads of the semiconductor device thereon, the image information items being stored in the storage means, thereby measuring a height from a bottom surface of each of all the leads of the semiconductor device to the transparent mounting plate.

BRIEF DESCRIPTION OF THE DRAWINGS

FIG. 13 illustrates horizontal edge intensity information obtained by executing the horizontal edge intensity detection processing shown in FIG. 9 on the image information shown in FIG. 12;

FIG. 14 illustrates vertical edge intensity information obtained by executing the vertical edge intensity detection processing shown in FIG. 9 on the image information shown in FIG. 12;

FIG. 15 illustrates horizontal edge position information obtained by executing the horizontal edge position detection processing on the horizontal edge intensity information shown in FIG. 13;

FIG. 16 illustrates vertical edge position information obtained by executing the vertical edge position detection processing on the vertical edge intensity information shown in FIG. 14;

FIG. 33 is a schematic view of the construction of a conventional lead flatness measurement apparatus.

DESCRIPTION OF THE PREFERRED EMBODIMENTS

First Embodiment

Figure 1:
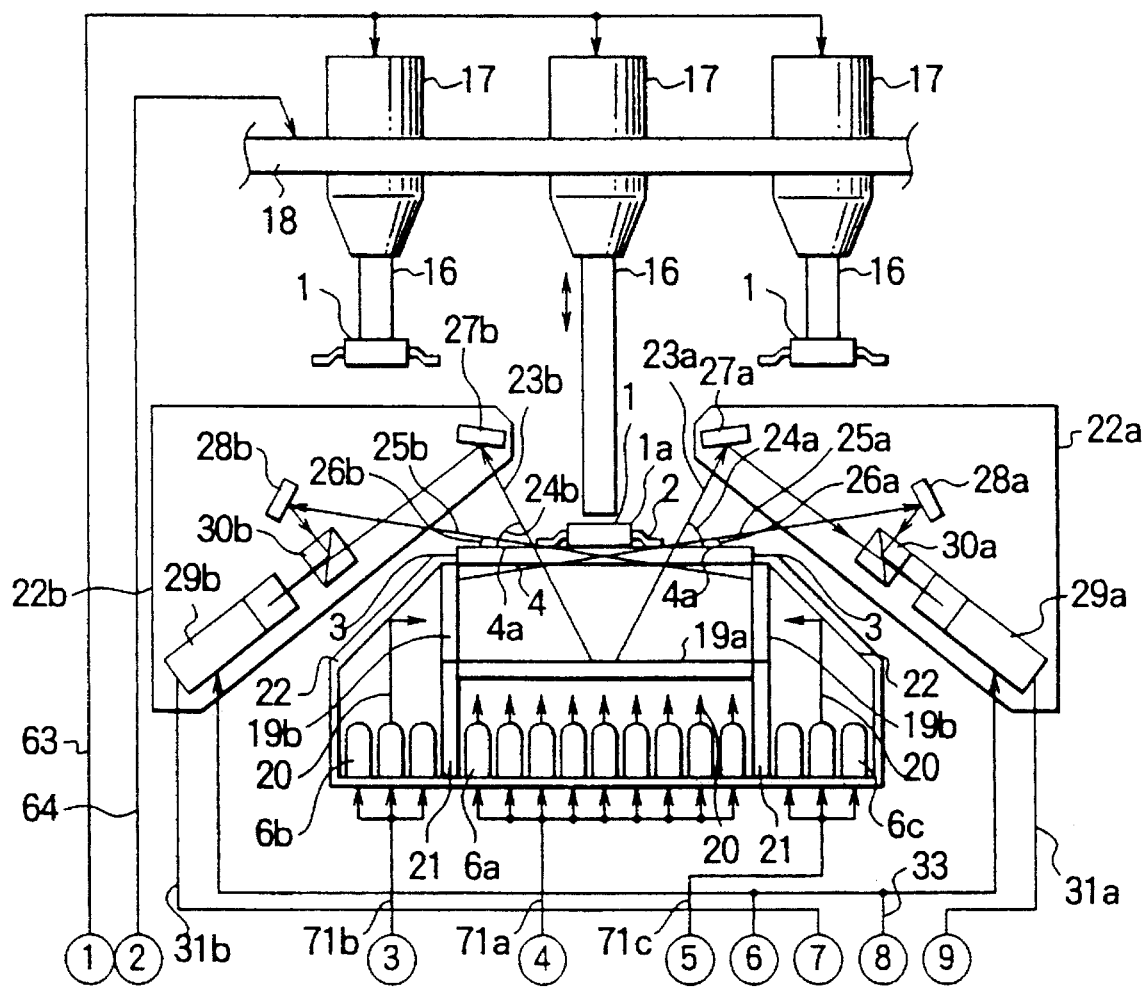
FIG. 1 is a schematic view of the construction of a measurement apparatus for measuring the dimensions of a semiconductor device according to a first embodiment of the present invention.
Figure 2:
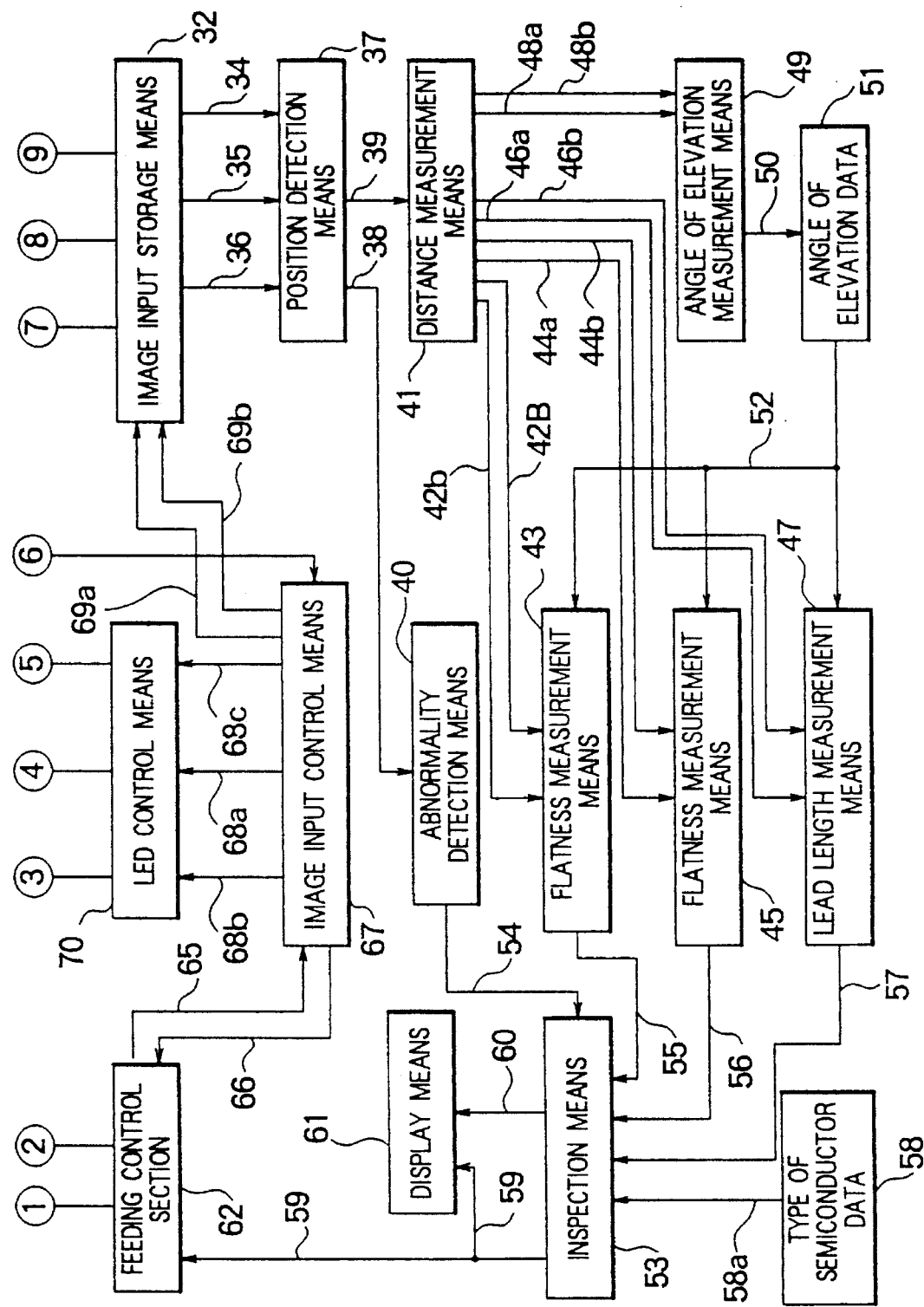
FIG. 2 illustrates the operation of the measurement apparatus shown in FIG. 1.

FIG. 1 is a schematic view illustrative of a measurement apparatus for measuring the dimensions of a semiconductor device according to a first embodiment of the present invention. FIG. 2 illustrates the operation of such a measurement apparatus. Referring to FIGS. 1 and 2, a plurality of leads 2 project from lateral surfaces of a package 1a of a surface mount semiconductor device 1. A suction head 16 lifts each of the semiconductor devices 1 using a vacuum. A suction head drive section 17 vertically moves each of the suction heads 16, and a feeding table 18 horizontally moves the suction head drive sections 17.

FIG. 1 shows a mounting base 3 for the semiconductor device 1 and a transparent mounting plate 4 fixed to the mounting base 3. A light-shielding band pattern 4a on the top surface of the transparent mounting plate 4 is placed outside the respective groups of the leads 2 projecting from the respective lateral surfaces of the semiconductor device 1 mounted on the mounting base 3 (See FIG. 23). The measurement apparatus comprises: a central LED illumination unit 6a arranged under the transparent mounting plate 4; a first LED illumination unit 6b arranged to one side of and below the transparent mounting plate 4; and a second LED illumination unit 6c arranged to another side of the below the transparent mounting plate 4 with the central LED illumination unit 6a between the first and second LED illumination units 6b and 6c. The measurement apparatus also comprises: a lower light-scattering plate 19a for scattering light 20 emitted from the central LED illumination unit 6a; lateral light-scattering plates 19b for respectively scattering the light 20 emitted from the first and second LED illumination units 6b and 6c; light-shielding plate 21 for shielding the light 20 from the central LED illumination unit 6a and the light 20 from the first LED illumination unit 6b and a light-shielding plate 21 for shielding the light 20 from the central LED illumination unit 6a and the light 20 from the second LED illumination unit 6c; and illumination reflecting plates 22 for reflecting the light 20 from the first and second LED illumination units 6b and 6c, respectively, so the light 20 impinges on the respective lateral scattering plates 19b.

A first optical section 22a is arranged on the reflecting side of the first LED illumination unit 6b along the axis of the lead 2 with respect to the semiconductor device 1, while a second optical section 22b is arranged on the opposite side of the semiconductor device 1 from the first optical section 22a. The respective optical sections 22a and 22b are placed to separately form images of the leads 2 on the lateral surface of the semiconductor device 1 mounted on the transparent mounting plate 4. First optical information items, i.e., light rays, 23a and 23b impinge on the first and second optical sections 22a and 22b, respectively, at larger first angles of elevation 24a and 24b with respect to the transparent mounting plate 4 along the axis of the leads 2 of the semiconductor device 1. Second optical information, i.e., light rays 25a and 25b impinge on the first and second optical sections 22a and 22b, respectively, at smaller second angles of elevation 26a and 26b.

The measurement apparatus further comprises: first optical information reflecting means 27a and 27b attached to the first and second optical sections 22a and 22b, respectively, for reflecting the respective first optical information items 23a and 23b; second optical information reflecting means 28a and 28b attached to the first and second optical sections 22a and 22b, respectively, for reflecting the respective second optical information 25a and 25b; a first imaging device 29a for receiving the first optical information 23a and the second optical information 25a; a second imaging device 29b for receiving the first optical information 23b and the second optical information 25b; and equi-distance optical reflection means 30a and 30b attached to the first and second optical sections 22a and 22b, respectively, for reflecting from the second optical information reflecting means 28a and 28b the respective second respective optical information items 25a and 25b. The distance between the lead group contained in the first and second optical information items 23a and 25a and the first imaging device 29a is equal to that between the lead group contained in the first and second optical information items 23b and 25b and the second imaging device 29b.

FIGS. 1 and 2 also indicate first image information 31a which is output from the first imaging device 29a; second image information 31b which is output from the second imaging device 29b; image input storage means 32 for receiving and storing the first and second image information items 31a and 31b, a synchronizing signal 33 which is output from the image input storage means 32; image information 34 which is output from the image input storage means 32 by means of an image information address 35 and an image information read-out signal 36; position detection means 37 for receiving the image information 34; abnormality information 38 which is output from the position detection means 37 and is input into abnormality detection means 40; position information 39 which is output from the position detection means 37 and is input into distance measurement means 41; first and second lead and light-shielding band pattern distance information 42a and 42b which are output from the distance measurement means 41 and input into flatness measurement means 43; first package and light-shielding band pattern distance information 44a which is obtained from the first optical information 23a and 23b and which is output from the distance measurement means 41 and input into stand-off measurement means 45; and second package and light-shielding band pattern information 44b obtained from the second optical information 25a and 25b and which is also output from the distance measurement means 41 and input into stand-off measurement means 45.

FIG. 2 further indicates: first lead and package distance information 46a which is obtained from the first optical information items 23a and 23b and which is output from the distance measurement means 41 and input into lead length measurement means 47; second lead and package distance information 46b which is similarly obtained from the second optical information items 25a and 25b and which is output from the distance measurement means 41 and input into lead length measurement means 47; first light-shielding pattern distance information 48a which is obtained from the first optical information items 23a and 23b and which is output from the distance measurement means 41 and input into angle-of-elevation measurement means 49; second light-shielding pattern distance information 48b which is similarly obtained from the second optical information items 25a and 25b and which is output from the distance measurement means 41 and input into angle-of-elevation measurement means 49; angle-of-elevation information 50 which is output from the angle-of-elevation measurement means 49; angle-of-elevation data 51 having the angle-of-elevation information 50 therein; and angle-of-elevation information 52 for each of the first and second optical sections 22a and 22b, which information 52 is output from the angle-of-elevation data 51 and input into the flatness measurement means 43, the stand-off measurement means 45 and the lead length measurement means 47.

Inspection means 53 receives therein detected abnormality information 54 which is output from the abnormality detection means 40, the flatness measurement information 55 which is output from the flatness measurement means 43, stand-off measurement information 56 which is output from the stand-off measurement means 45, lead length measurement information 57 which is output from the lead length measurement means 47, and known information 58a about the type of semiconductor, which information 58a is stored as type-of-semiconductor data 58. The inspection means 53 also outputs inspection results 59 and measurement results 60. Display means 61 display the inspection results 59 and the measurement results 60.

Feeding control section 62 outputs a suction head control signal 63 for controlling the suction head drive section 17 and a feeding table control signal 64 for controlling the feeding table 18. The feeding control section 62 also receives the inspection results 59 and outputs a semiconductor-device mounting signal 65 so as to further receive an image input completion signal 66. Image input control means 67 receives the mounting signal 65 and the synchronizing signal 33 and outputs a central LED luminous signal 68a, first and second LED luminous signals 68b and 68c, and first and second image information input signals 69a and 69b. LED control means 70 receives the central LED luminous signal 68a and the first and second LED luminous signals 68b and 68c. The LED control means 70 also outputs a central LED control signal 71a to the central LED illumination unit 6a and outputs first and second LED control signals 71b and 71c to the first and second LED illumination units 6b and 6c, respectively.

A brief explanation will now be given of the operation of the semiconductor-device measurement apparatus constructed as described above.

Figure 3:
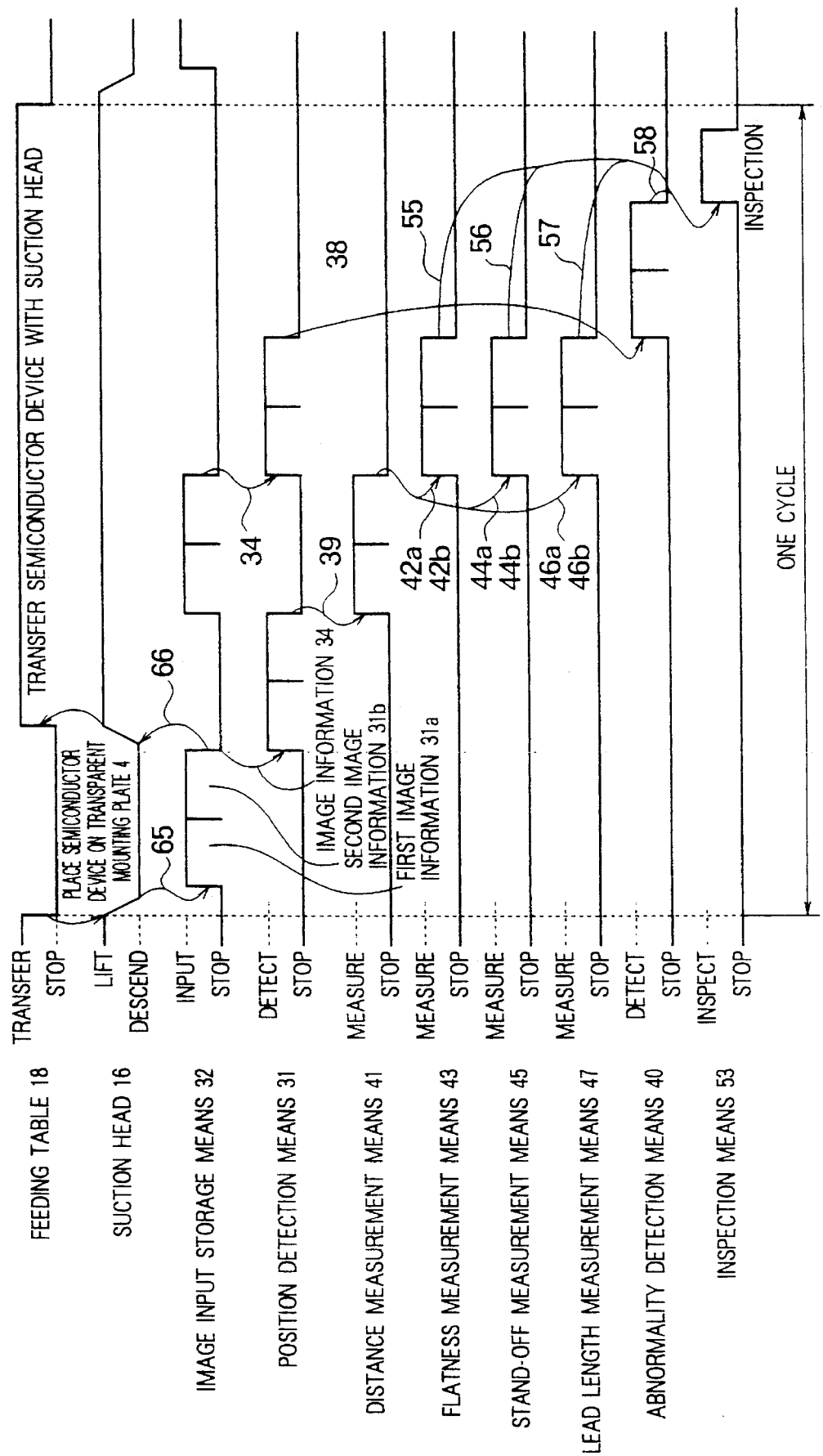
FIG. 3 is a timing chart illustrative of the operation of one cycle of the measurement apparatus shown in FIG. 1.
Figure 4:
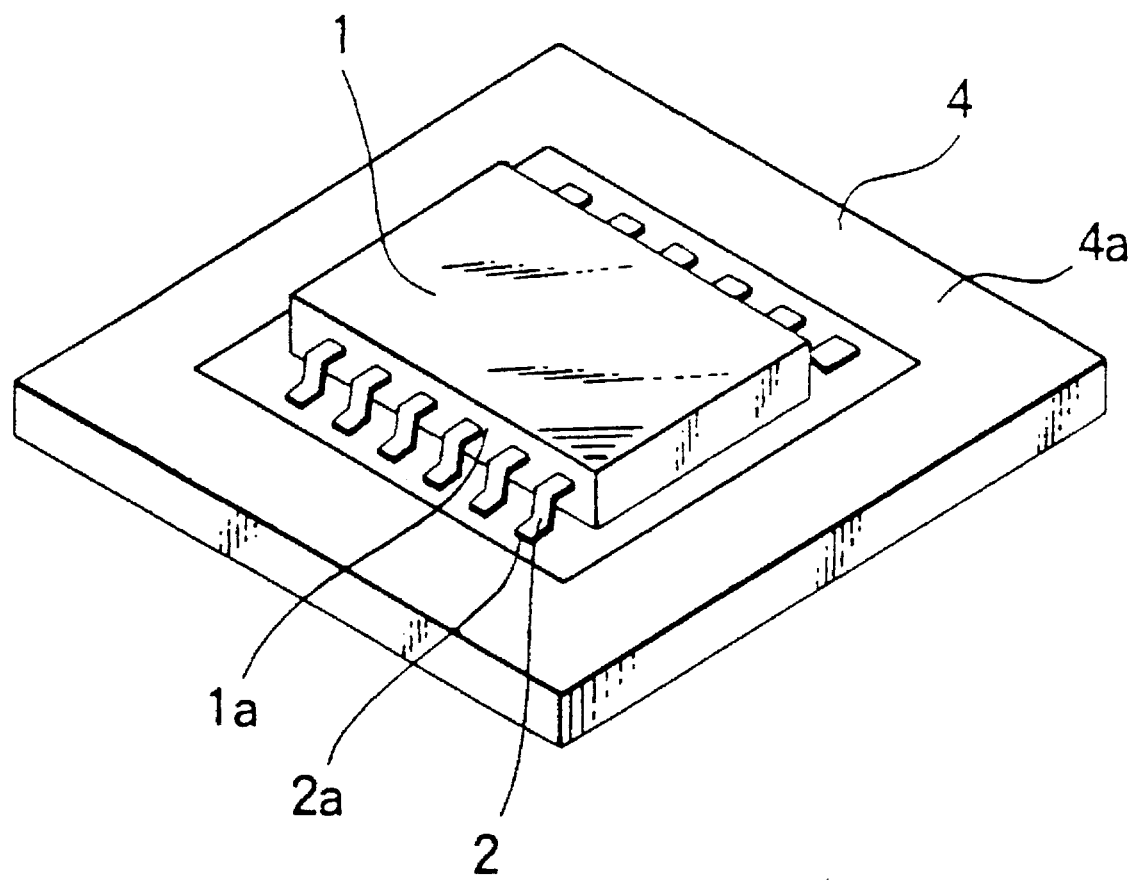
FIG. 4 is a perspective view of the semiconductor device placed on a transparent mounting plate.

FIG. 3 is a timing chart illustrative of the operation of one cycle of the semiconductor-device measurement apparatus. Referring to FIGS. 2 and 3, the feeding control section 62 controls the suction head drive section 17 through the suction head control signal 63 and controls the feeding table 18 through the feeding table control signal 64. The feeding table 18 feeds the semiconductor device 1 which has been lifted by the suction head 16, together with the suction head drive section 17. The suction head drive section 17 lowers the suction head 16 downward so as to release the semiconductor device 1 from the suction force and to place it on the transparent mounting plate 4 (See FIG. 4). Simultaneously, the semiconductor-device mounting signal 65 is input into the image input control means 67 from the feeding control section 62. Upon input of the mounting signal 65, the image input control means 67 outputs the respective LED luminous signals 68a–68c. The LED control means 70 controls the on/off state of the LED illumination units 6a–6c through the respective LED control signals 71a–71c. The image input control means 67 outputs the first image information input signal 69a and allows the image input storage means 32 to store the first image information 31a therein. Upon completion of storing the first image information 31a, the image input control means 67 sequentially outputs the second image information input signal 69b and permits the image input storage means 32 to store the second image information 31b therein. Upon completion of storing the first and second image information items 31a and 31b, the image input control means 67 outputs the image input completion signal 66 to the feeding control section 62. The feeding control section 62 controls the suction head drive section 17 through the suction head control signal 63 so as to permit the suction head 16 to lift the semiconductor device 1 and to allow the suction head drive section 17 to lift the semiconductor device 1 upward. The semiconductor device 1 is further fed, together with the suction head drive section 17 and the suction head 16, through the feeding table control signal 64, and a subsequent semiconductor device 1 is fed onto the transparent mounting plate 4.

Subsequently, the position detection means 37 detects, from the first image information 31a stored in the image input storage means 32, coordinates of the lateral surface of the package 1a, and the end surface 2a of the lead 2 and the light-shielding band pattern 4a, while it detects, from the second image information 31b stored in the image input storage means 32, coordinates of the lateral surface of the package 1a, the end surface 2a of the lead 2 and the light-shielding band pattern 4a, thereby outputting the position detection signal 39 to the distance measurement means 41. The distance measurement means 41 measures, from the respective image information items 31a and 31b, the distance from the lead end 2a to the light-shielding band pattern 4a contained in the first optical information 23 and the distance from the lead end 2a to the light-shielding band pattern 4a contained in the second optical information 25, according to the position detection signal 39. The distance measurement means 41 thus outputs the first and second lead and light-shielding band pattern distance information items 42a and 42b to the flatness measurement means 43. Moreover, according to the position detection signal 39, the distance measurement means 41 measures, from the respective image information items 31a and 31b, the distance from the lateral surface of the package 1a to the light-shielding band pattern 4a contained in the first optical information 23 and the distance from the lateral surface of the package 1a to the light-shielding band pattern 4a contained in the second optical information 25. The distance measurement means 41 thus outputs the first and second package and light-shielding band pattern distance information items 44a and 44b to the flatness measurement means 43.

Further, according to the position detection signal 39, the distance measurement means 41 measures, from the respective image information items 31a and 31b, the distance from the lead end 2a to the package 1a contained in the first optical information 23 and the distance from the lead end 2a to the package 1a contained in the second optical information 25. The distance measurement means 41 thus outputs the first and second lead and package distance information items 46a and 46b to the flatness measurement means 43. Then, the flatness measurement means 43 measures the flatness of a group of leads from the angle-of-elevation information 52 from each of the first and second optical sections 22a and 22b, which information 52 is stored as the distance data 51, and the first and second lead and light-shielding band pattern distance information items 42a and 42b so as to output the flatness measurement information 55 to the inspection means 53. The stand-off measurement means 45 measures the stand-off characteristics peculiar to the lateral surface of the package 1a from the angle-of-elevation information 52 about each of the first and second optical sections 22a and 22b, which information 52 is stored as the distance data 51, and the first and second package and light-shielding band pattern distance information 44a and 44b so as to output the stand-off measurement information 56 to the inspection means 53. The lead length measurement means 47 measures the lead length from the angle-of-elevation information 52 from each of the first and second optical sections 22a and 22b, which information 52 is stored as the distance data 51, and the first and second lead and package distance information 46a and 46b so as to output the lead length measurement information 57 to the inspection means 53.

Meanwhile, upon completion of the operation by the position detection means 37, if there is no semiconductor device 1 on the mounting plate 4, the first and second information items 31a and 31b are stored in the image input storage means 32 in a manner as described above. Subsequently, the position detection means 37 detects the location where an abnormality occurs in the first and second image information items 31a and 31b so as to output the abnormality information 38 to the abnormality detection means 40. In response to this, the abnormality detection means 40 measures the dimensions of such abnormal matter from the abnormality information 38 so as to output the detected abnormality information 54 to the inspection means 53.

The inspection means 53 then inspects the flatness measurement information 55, the stand-off information 56, the lead length measurement information 57 and the detected abnormality information 54 from the type-of-semiconductor information 58a which is output from the type-of-semiconductor data 58 so that the inspection results 59 and the measurement results 60 can be displayed by the display means 61. According to the inspection results 59, the feeding means 62 suspends the movement of the feeding table 18 and changes storage sections (not shown) where the semiconductor device 1 is accommodated.

Figure 5:
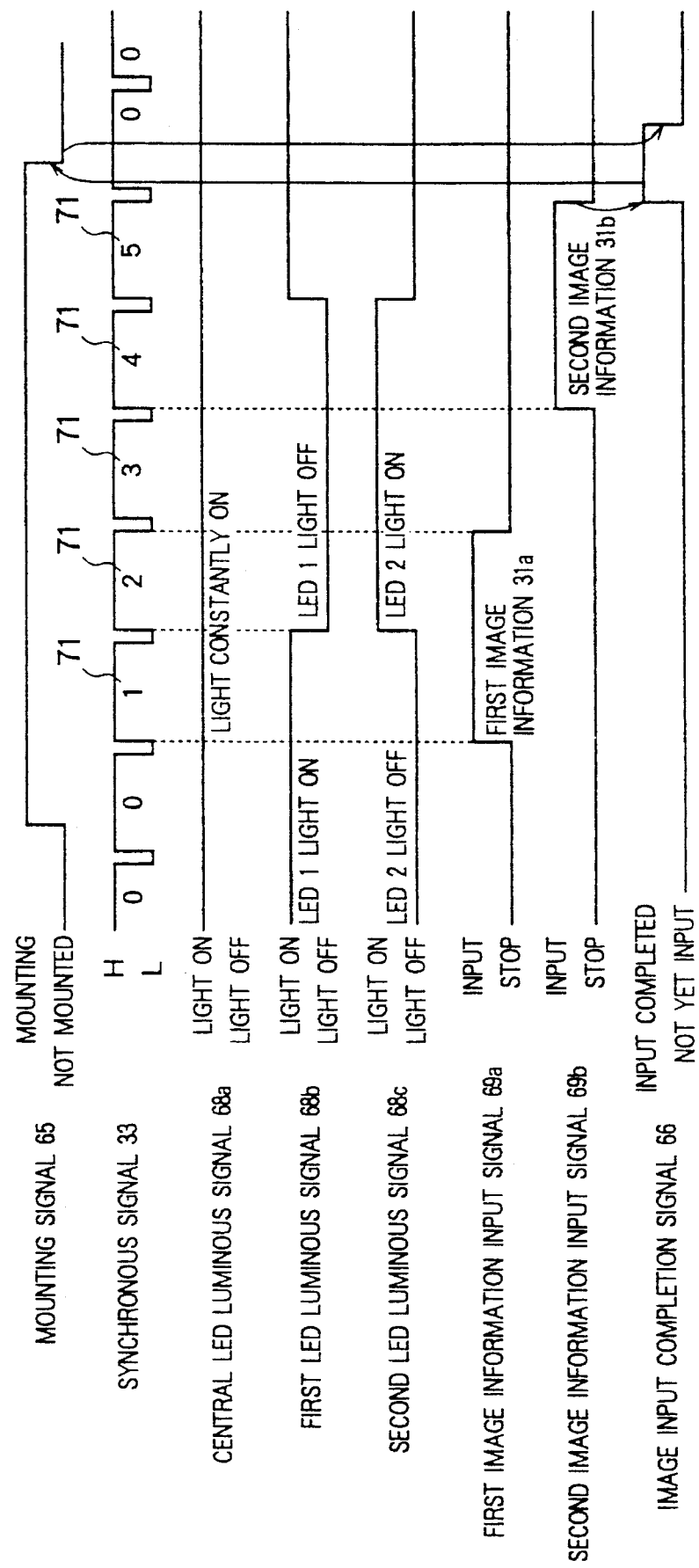
FIG. 5 is a timing chart illustrative of the input operation of image information performed by image information control means.

A description will further be given with reference to the timing chart of FIG. 5 of the light emission of the LED illumination unit 6 by the image input control means 67 and the operation of the image information 31 input into the image input storage means 32. The image input control means 67 is allowed to start counting from the moment at which the semiconductor-device mounting signal 65 is changed from "NOT MOUNTED" to "MOUNTING" and counts how many times the synchronizing signal 33 is changed from "L" into "H". The image input control means 67 permits the central LED luminous signal 68a to constantly remain in the "ON" state. The image input control means 67 turns off the first LED luminous signal 68b and turns on the second LED luminous signal 68c when a count value 11 becomes "2", while it turns on the first LED luminous signal 68b and turns off the second LED luminous signal 68c when the count value 71 becomes "5". The image input control means 67 allows the first image input signal 69a to go into the "INPUT" mode when the count value 71 becomes "1", and interrupts the first image input signal 69a when the count value becomes "2" and when the synchronizing signal 33 changes from "H" into "L". The image input control means 67 also permits the second image input signal 69b to go into the "INPUT" mode when the count value 71 becomes "4", and interrupts the second image input signal 69b when the count value 71 becomes "5" and when the synchronizing signal 33 changes from "H" into "L", thereby simultaneously completing the input of the image input completion signal 66.

The feeding control section 62 moves the semiconductor device 1 from the transparent semiconductor-device mounting plate 4 upon completion of the input of the input completion signal 66 so as to switch the mounting signal 65 to "NOT MOUNTED". When the mounting signal is switched to "NOT MOUNTED", the image input control means 67 clears the count value 71 and switches the input completion signal 66 to "NOT YET".

Figure 6:
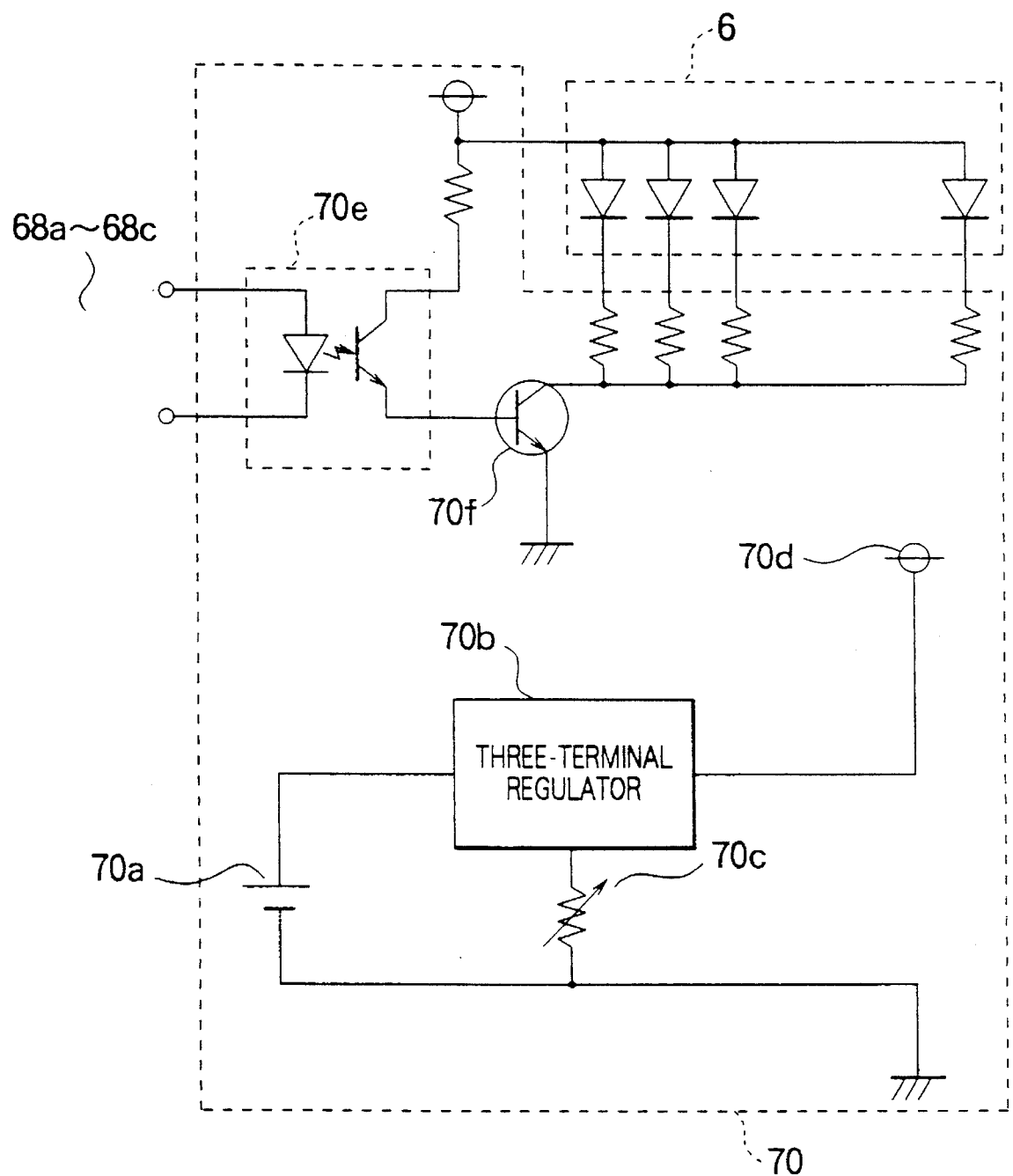
FIG. 6 is a circuit diagram illustrative of LED control means.

An explanation will further be given of the operation of the LED control means 70 with reference to FIG. 6. In the LED control means 70, an LED power supply 70d at an arbitrary voltage can be obtained from a constant-voltage power supply 70a through a three-terminal regulator 70b and a variable resistor 70c. The LED luminous signal 68 is isolated in a photocoupler 70e so as to be input into a transistor 70f. The LED control means 70 controls the on/off states of the LED illumination unit 6 by means of the transistor 70f and controls the luminous output by means of the variable resistor 70c.

Figure 7:
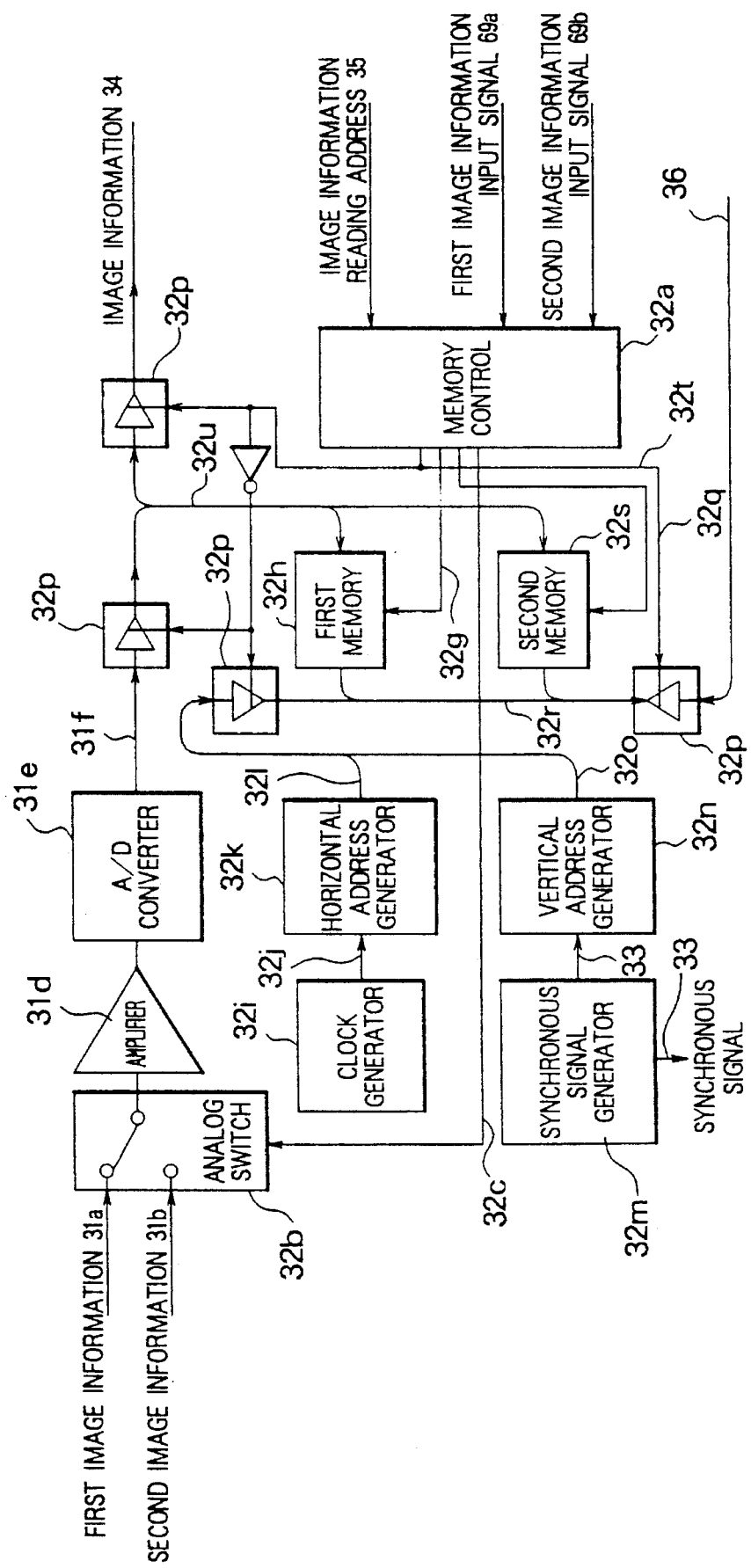
FIG. 7 is a block diagram illustrative of image input storage means.

The operation of the image input storage means 32 will now be described with reference to FIG. 7. When the first image information input signal 69a is switched to "INPUT", an image information selection signal 32c is input into an analog switch 32b from a memory control 32a, thereby selecting the first image information 31a. The first image information 31a in the form of an analog value, is amplified in an amplifier 31d so as to be converted into a digital value 31f in an A/D converter 31e. Further, a first memory 32h is selected by a first control signal 32g which is output from the memory control 32a and the first memory 32h is also switched to the state in which data is written thereinto. A horizontal address 32l is output from a horizontal address generator 32k in response to a clock signal 32j which is output from a clock generator 32i. On the other hand, a vertical address 32o is output from a vertical address generator 32n in response to the synchronizing signal 33 which is output from a synchronizing signal generator 32m. In the tristate buffers 32p, the input terminal of the image information 31 is selected through a switching signal 32q which is output from the memory control 32a. The first memory 32h stores the digitized first image information 31a by means of an address 32r obtained by combining the horizontal address 32l and the vertical address 32o until the first image information input signal 69a is interrupted. The operation of storing the second image information 31b by the second memory control 32s is similar to that of the first image information 31a, and an explanation thereof will thus be omitted.

Moreover, when the image information read-out signal 36 is input into the memory control 32, either of the first memory 32h or the second memory 32s is selected through either of the corresponding first control signal 32g or the corresponding second control signal 32t by means of this image information read-out signal 36. The selected memory is switched to the state in which the data is read out therefrom. In the tristate buffers 32p, the output terminal of the image information is selected through the switching signal 32q. The storage means 32 reads out the image information 32u from one of the memories 32h and 32s according to the image information address 35 so as to output the storage image information 34. Also, the storage means 32 outputs the synchronizing signal 33 from the synchronizing signal generator 32m.

Figure 8:
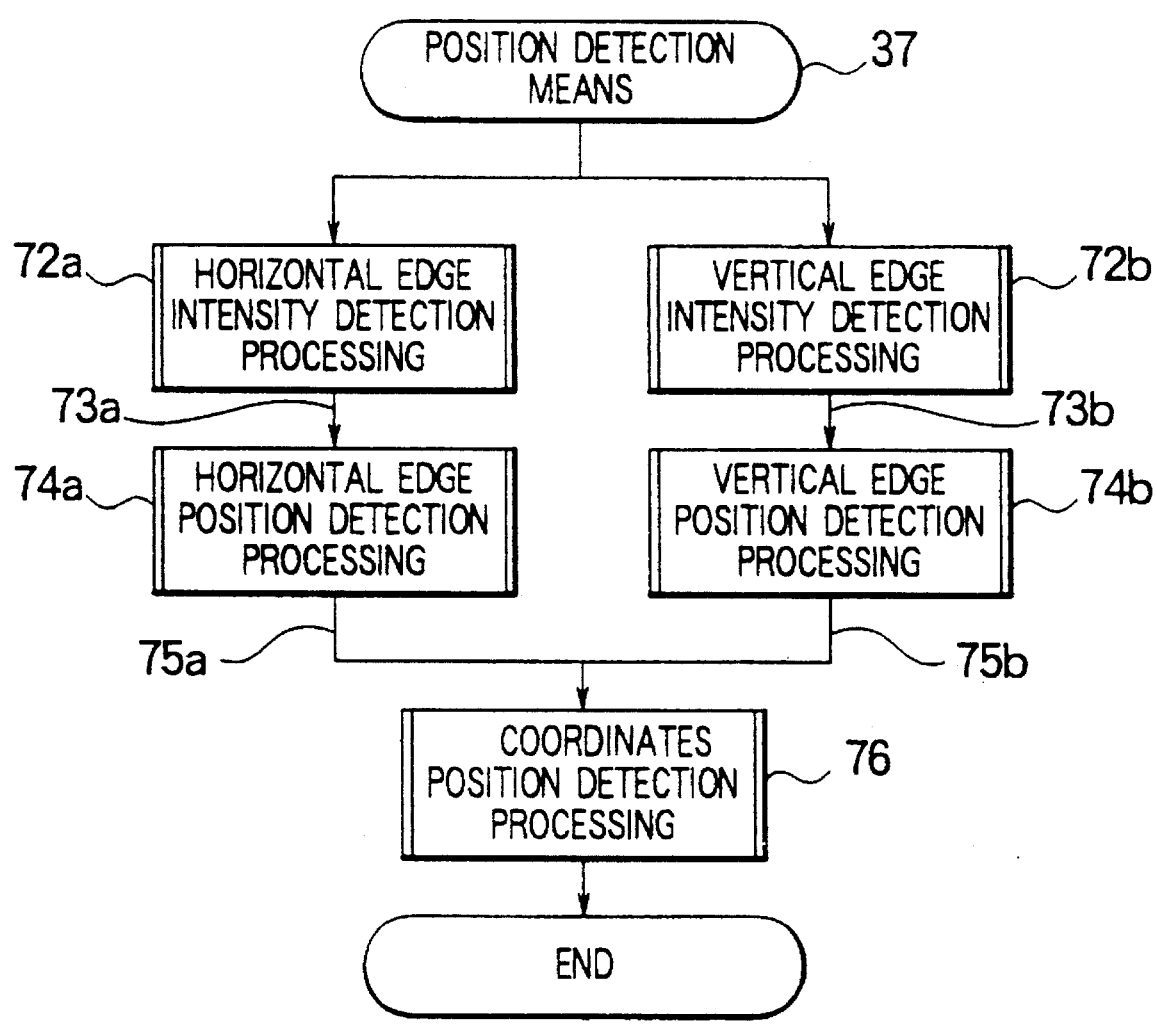
FIG. 8 is a flow chart illustrative of the overall schematic operation of position detection means.

The operation of the position detection means 37 will now be described. FIG. 8 is a flow chart illustrative of the overall operation of the position detection means 37. Referring to FIG. 8, horizontal edge intensity information 73a is output from the image information 31 through the detection processing 72a of the horizontal edge intensity. At the same time, vertical edge intensity information 73b is output from the image information 31 through detection processing 72b of the vertical edge intensity information. Successively, horizontal edge position information 75a is output from the horizontal edge intensity information 73a through detection processing 74a of the horizontal edge position. At the same time, vertical edge position information 75b is output from the vertical edge intensity information 73b through detection processing 74b of the vertical edge position. Further, the detected position information 39 is output from the horizontal edge position information 75a and the vertical edge position information 75b through detection processing 76 of the coordinates position.

Figure 9:
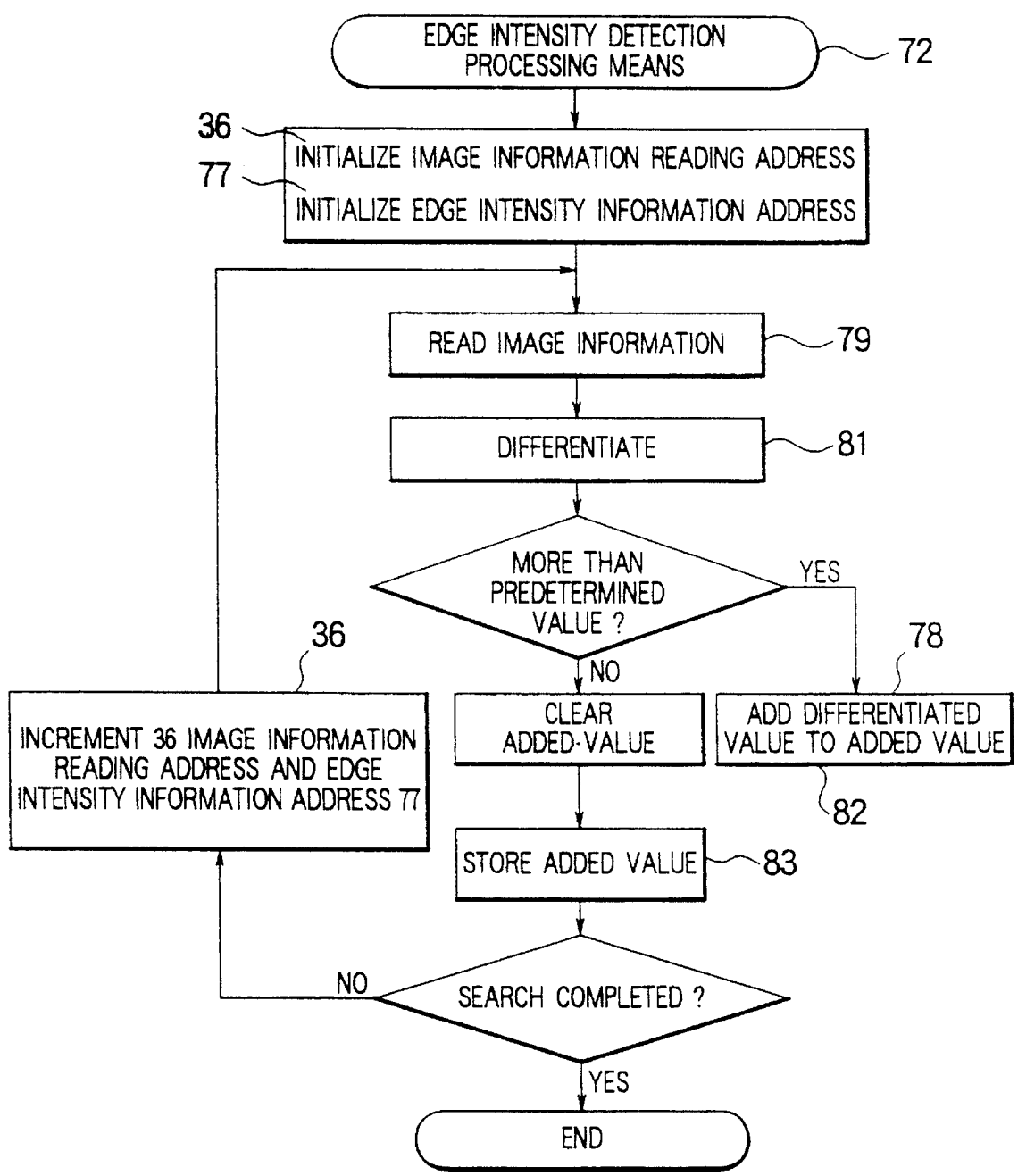
FIG. 9 is a flow chart illustrative of the operation of edge intensity detection processing.

FIG. 9 is a flow chart illustrative of operation of edge intensity detection processing means 72, more specifically, illustrative of either of the horizontal edge intensity detection processing 72a or the vertical edge intensity detection processing 72b. Referring to FIG. 9, the edge intensity detection processing means 72 first initializes the image information read-out address 35 and edge intensity read-out address 77 and sets added value 78 to be "0". Then, one pixel 80 of the image information 34 which is positioned at the image information address 35 and one pixel of the image information 34 which is positioned at an address subsequent to the image information address 35 are read out through image information reading 79. The difference between those two items of image information 34 is thus calculated through differentiation 81. Then, the thus-obtained differentiated value 82 is compared with a predetermined value 82a. If the former is greater than the latter, the differentiated value 82 is added to the above-mentioned added value 78. If the former is not greater than the latter, the added value 78 is set to be "0". Then, this added value 78 is stored in the position of the edge intensity information address 77 of the edge intensity information 73 as an added value storage 83. Subsequently, if the foregoing operation has been completed over the overall image information, the edge intensity detection processing ends. If not, the image information read-out address 35 and the edge intensity information address 77 are each incremented by one, and the flow returns prior to the image information reading 79.

Figure 10:
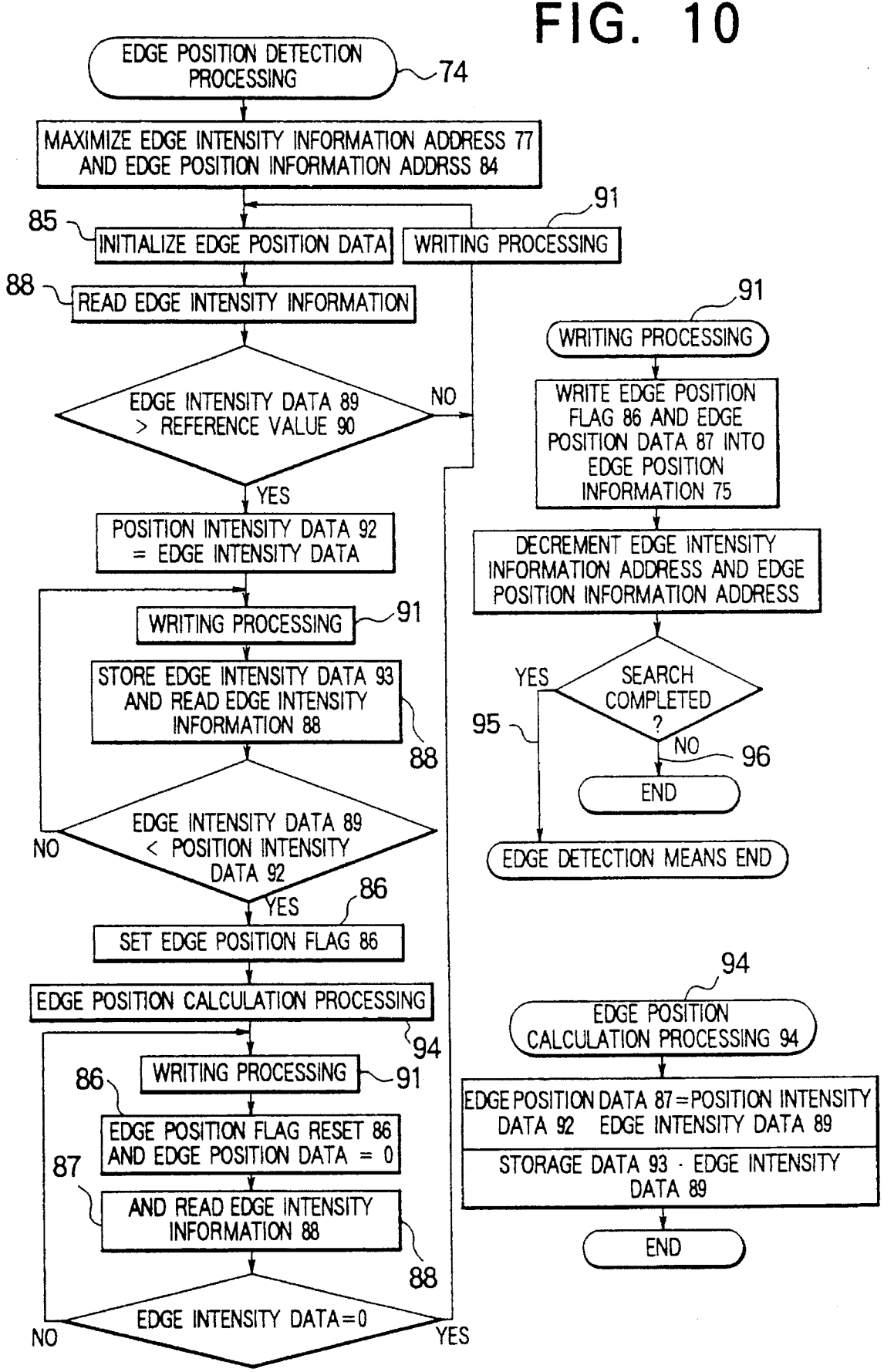
FIG. 10 is a flow chart illustrative of the operation of edge position detection processing.

FIG. 10 is a flow chart illustrative of the edge position detection processing 74, and, more specifically, illustrative of the operation of either of the horizontal edge position detection processing 74a or the vertical edge position detection processing 74b. Referring to FIG. 10, the edge intensity information address 77 and an edge position information address 84 are first maximized. Then, an edge position flag 86 is reset through edge position data initialization 85, and edge position data is set to be "0". Subsequently, one pixel 80 of the edge intensity information 73 positioned at the edge position information address 77 is read into edge intensity data 89 through edge intensity information reading 88. The thus-obtained edge intensity data 89 is compared with a predetermined value 90. If the former is not greater than the latter, writing processing 91 is executed, and the flow returns to the edge position data initialization 85. If the former is greater than the latter, one-half of the value of the edge intensity data 89 is set as the position intensity data 92.

Then, the writing processing 91 is executed. The edge intensity data 89 is stored in storage data 93, and the edge intensity information reading 88 is executed. This edge intensity data 89 is compared with the position intensity data 92. If the former is not smaller than the latter, the flow returns to the previous writing processing 91. If the former is smaller than the latter, the edge position flag is set, and edge position calculation processing 94 is executed. Then, the writing processing 91 is executed. Subsequently, the edge position flag 86 is reset, and the edge position data 87 is reset to be "0", followed by the edge position information reading 88. If the edge intensity data 89 is "0", the writing processing 91 is executed, and the flow returns to the edge position data initialization 85. If the edge intensity data 89 is not "0" the flow returns to the writing processing 91 subsequent to the edge position calculation processing 94. The writing processing 91 is executed as follows. The edge position flag 86 and the edge position data 87 are stored in the position of the edge position information address 84 of the edge position information 75. Then, the edge intensity information address 77 and the edge position information address 84 are each decremented by one. If the edge position detection 74 has been completed over the entire edge intensity information address 77, the completion 95 of the edge position detection processing is executed. If not, the completion 96 of the writing processing is executed. The following equation 1 is calculated by the edge position detection processing 94. The edge position data shall be a value smaller than 1.

Edge position data 87 = $\qquad$ Equation 1

(position intensity data 92 − edge intensity data 89)/

(storage data 93 − edge intensity data 89)

Figures 11, 12:
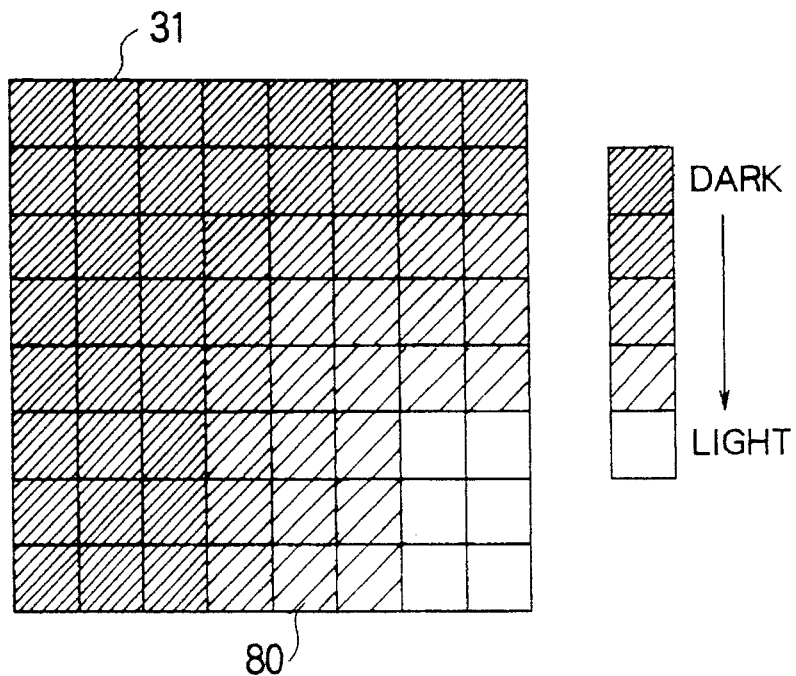
FIG. 11 is a partial enlarged view of analog image information.
FIG. 12 illustrates one example of image information obtained by digitizing the analog image information shown in FIG. 11.

FIG. 11 is a partially enlarged view of one example of the analog image information 31 which is input into the storage means 32. One square of the image information 31 represents one pixel 80 and the brightness is shown per square measure. FIG. 12 illustrates the stored image information 34 in the form of digitized values 31d per square measure, which digitized values are obtained by digitizing the analog image information shown in FIG. 11 in the storage means 32. FIG. 13 illustrates the horizontal edge intensity information 73a resulting from executing the horizontal edge intensity detection processing 72a horizontally from left to right on the stored image information 34 shown in FIG. 12. FIG. 14 illustrates the vertical edge intensity information 73b resulting from executing the vertical edge intensity detection processing 72b vertically from top to bottom on the intensity image information 34 shown in FIG. 12. FIG. 15 is the horizontal edge position information 75a obtained by executing the horizontal edge position detection processing 74a horizontally from right to left on the horizontal edge intensity information 73a shown in FIG. 13. The upper stage and lower stage of two consecutive values of such horizontal edge position information 75a show the edge position flag 86 and the edge position data 87, respectively. FIG. 16 illustrates the vertical edge position information 75b obtained by executing the vertical edge position detection processing 74b vertically from bottom to top on the vertical edge intensity information 73b shown in FIG. 12. The upper and lower stages of two consecutive values of such vertical edge position information 75b show the edge position flag 86 and the edge position data 87, respectively.

An explanation will now be given of a position detection method whereby accuracy can be obtained in a degree smaller than one pixel according to an image shading process. In this method an edge is found from a position in which an image starts to change from light to dark or from dark to light.

Figure 17A:
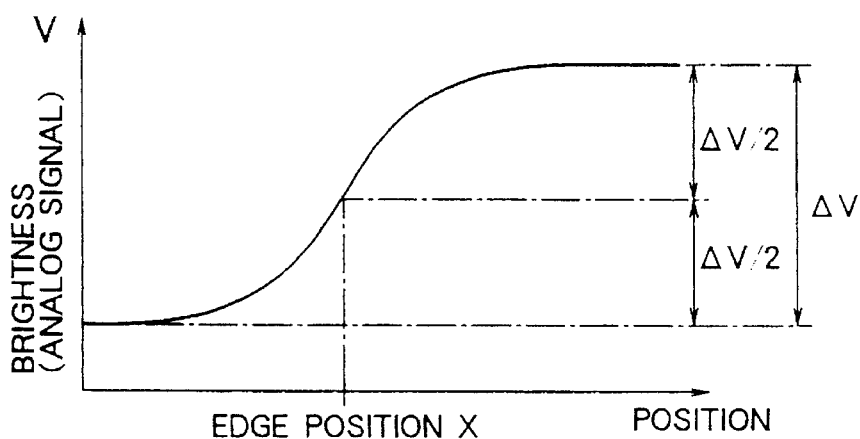
FIGS. 17A–17D are diagrams illustrative of a position detection method whereby accuracy smaller than one pixel is obtained using an image shading process.

As is seen from FIG. 17A, an edge is defined by the position in which the image is brightened by one-half ($\Delta V/2$) of the variance amount ($\Delta V$) in changing the brightness from light to dark or from dark to light. According to the positions and brightness of such an edge and the two adjacent preceding and subsequent pixels, the position of this edge is detected by a sub-pixel. According to this method, the edge position can be detected to an accuracy of ¼ pixel.

Figure 17B:
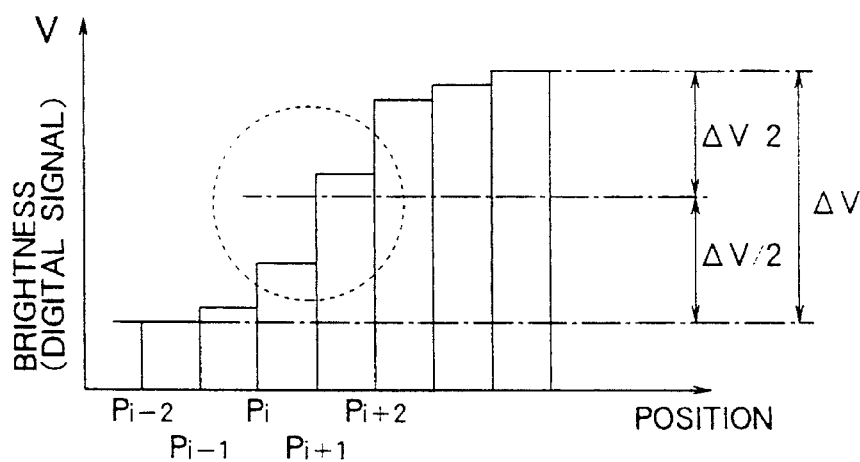
Figure 17C:
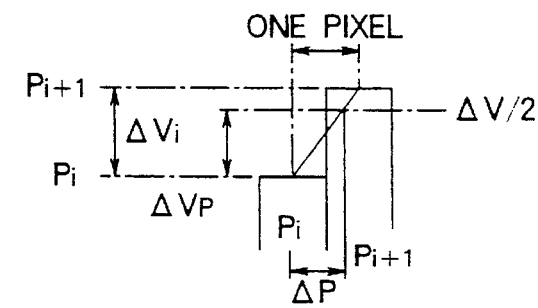
Figure 17D:
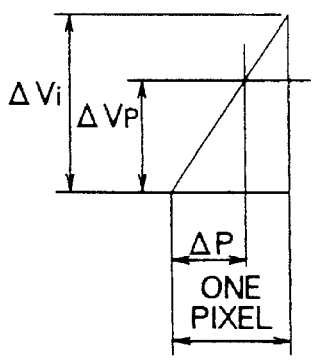

FIG. 17A is a diagram illustrative of the relationship between the position and the brightness of the analog image information. FIG. 17B is a diagram illustrative of this relationship in a digitized form. Further, FIG. 17C is a partially enlarged diagram of the relationship shown in FIG. 17B. The edge position x is defined by the coordinates of the point of intersection interconnecting the brightness of the $\Delta V/2$ line and the lines of the two adjacent pixels $P_i$, $P_{i+1}$. Hence, as is seen from FIG. 17D, the edge position x can be obtained by the equation: $\Delta P =$ one pixel $\times \Delta V_p/\Delta V_i$, that is, the edge position x = $P_i+\Delta P$. It can be understood that the edge position can be detected to accuracy of smaller than one pixel.

Figure 18:
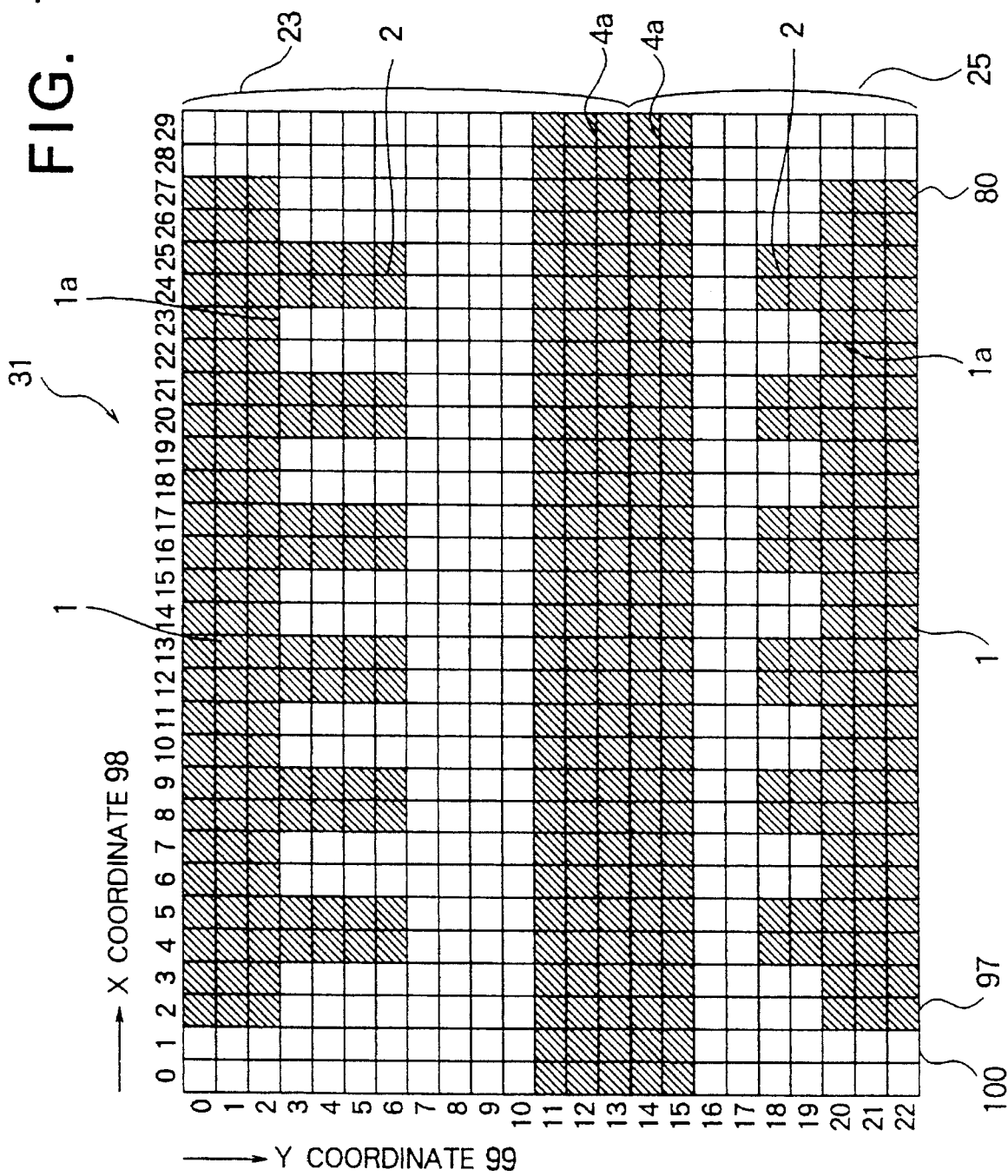
FIG. 18 schematically illustrates one example of image information.

A description will now be given of the coordinate position detection processing 76. FIG. 18 illustrates one example of the image information 31. Referring to FIG. 18, the image information 31 includes upper and lower image information items obtained from the first and second optical information items 23 and 25, respectively. The second optical information item 25 is vertically reversed by the optical reflecting means 30 with respect to the first optical information item 23. Dark portions 97 correspond to the semiconductor device 1 and the light-shielding band pattern 4a. A square measure indicates one pixel 80 and represents X coordinate 98 from left to right and Y coordinate 99 from top to bottom. Reference numerals 100 and 97 indicate light portions and dark portions, respectively.

Figure 19:
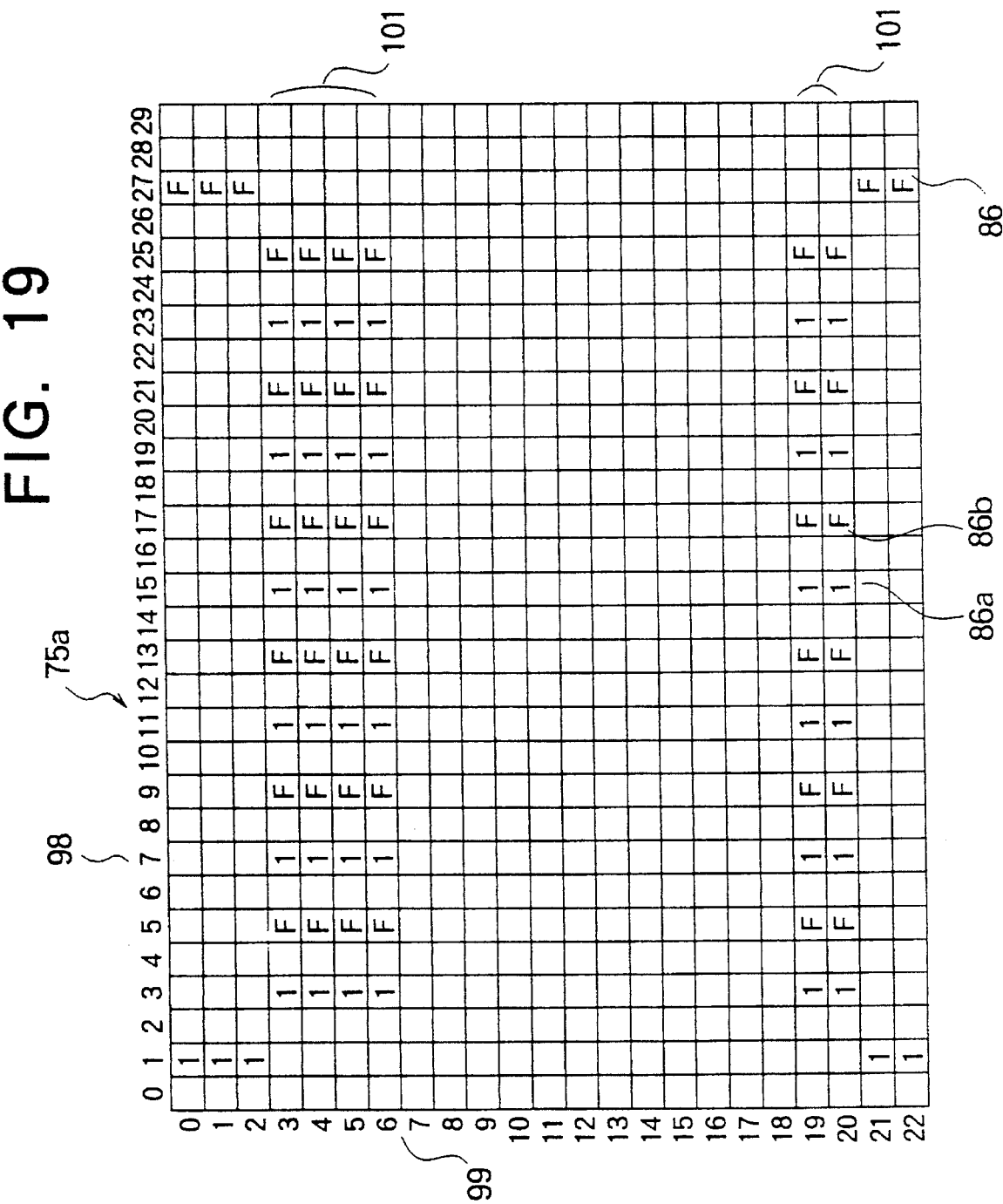
FIG. 19 schematically illustrates horizontal edge position information obtained by executing the horizontal edge position detection processing on the image information shown in FIG. 18.

FIG. 19 illustrates one example of the horizontal edge position information 75a obtained by executing the horizontal edge intensity detection processing 72a and the horizontal edge position detection processing 74a on the image information 31 shown in FIG. 18. The value "1" within a square indicates the edge position flag 86a indicative of a change from light to dark, while "F" indicates the edge position flag 86b indicative of a change from dark to light. The portions filled in with nothing correspond to "0" in FIG. 19, free from edges. The edge position data 87 is omitted in FIG. 19.

Figure 20:
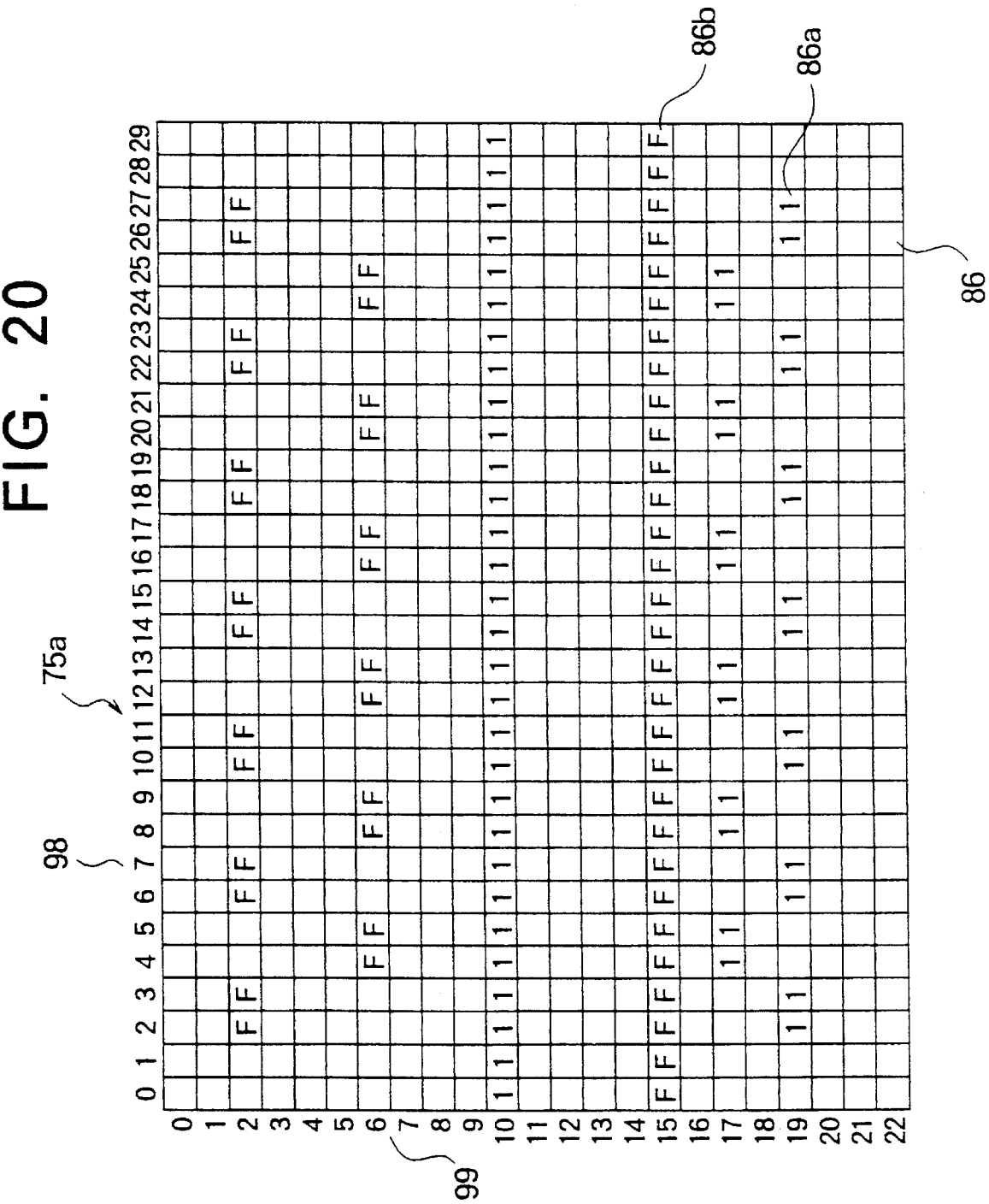
FIG. 20 schematically illustrates vertical edge position information obtained by executing the vertical edge position detection processing on the image information shown in FIG. 18.

FIG. 20 illustrates one example of the vertical edge position information 75b obtained by executing the vertical edge intensity detection processing 72b and the vertical edge position detection processing 74b on the vertical edge position information 76b. The value "1" within a square indicates the edge position flag 86a indicative of a change from light to dark, while "F" indicates the edge position flag 86b indicative of a change from dark to light. The portions filled in with nothing correspond to "0" in FIG. 20, free from edges. The edge position data 87 is omitted in FIG. 20.

Figure 21:
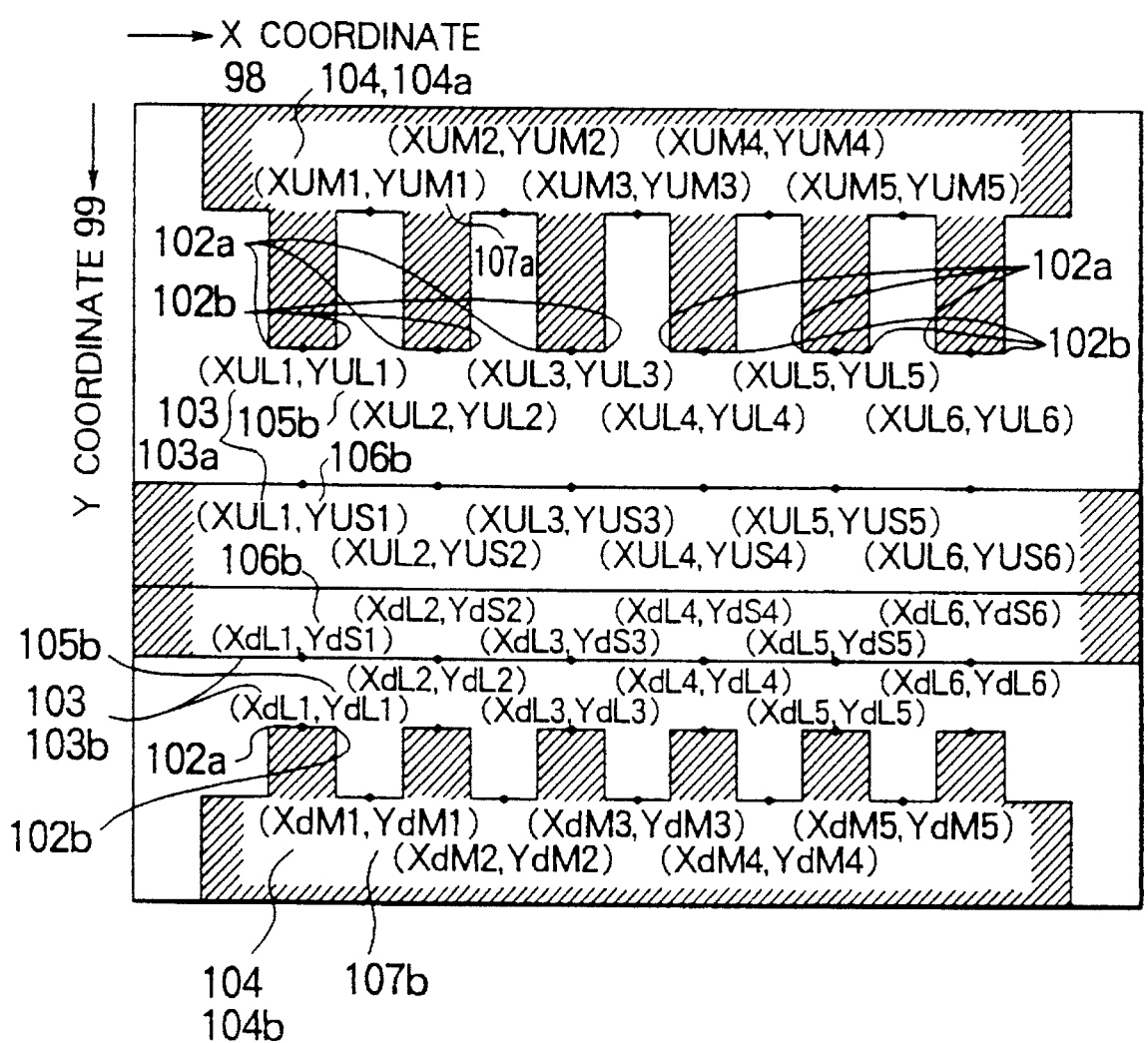
FIG. 21 a schematic diagram obtained by overlapping the detected position information over the image information shown in FIG. 18.

In the horizontal edge position information 75a shown in FIG. 19, a portion in which the edge position flag 86 changes between "0" and "F" indicates the presence of the lead 2. A portion located between "1" and "F" represents a lead section 2, while a portion placed between "F" and "1" shows a package section 1a. The number of the lead sections 2 corresponds to the number of the leads 2 of one group arranged on one lateral surface of the semiconductor device 1. There are six leads 2 in the example shown in FIG. 19. FIG. 21 illustrates left-hand coordinates 102a obtained by adding the X coordinates 98 when the edge position flag 86 is "1" to the edge position information 87 about such X coordinates 98. FIG. 21 also illustrates right-hand coordinates 102b obtained by adding the X coordinates 98 when the edge position flag 86 is "0" to the edge position information 87 about such Y coordinates. The lead X coordinate 103 is obtained by adding the left-hand coordinates 102a to the adjacent right-hand coordinates 103b on the right and by dividing the resultant value by two. On the other hand, the package X coordinate 104 is obtained by adding the right-hand coordinates 102b to the adjacent left-hand coordinate 102a on the left and by dividing the resultant value by two. It will be assumed that the group of the first lead X coordinates 103a and the group of the first package coordinates 104a are obtained from the first optical information 23, while the group of the second lead X coordinates 103b and the group of the second package X coordinates 104b are obtained from the second optical information 25.

In the vertical edge position information 75b shown in FIG. 20, searching is performed vertically from top to bottom along the Y axis 99 with respect to integers of the first lead X coordinates 103a. The Y coordinate 99 when the edge position flag 86 is "F" is found through this searching. A first lead Y coordinate 105a can thus be found by adding the above-mentioned Y coordinate 99 when the edge position flag 86 is "F" to the edge position data 87 about such a Y coordinate 99. Searching is further performed to find the Y coordinate 99 when the edge position flag 86 is "1". A first Y coordinate 106a of the light-shielding band pattern 104a is obtained by adding the above-mentioned Y coordinate 99 when the edge position flag is "1" to the edge position data 87 on such a Y coordinate 99. The thus-obtained first light-shielding band pattern Y coordinate 106a corresponds to the first package X coordinate 104a in the form of an integer. Searching is performed along the Y axis 99 vertically from top to bottom so as to find the Y coordinate 99 when the edge position flag 86 is "F". A first package Y coordinate 107a is obtained by adding the above-mentioned Y coordinate 99 when the edge position flag is "F" to the edge position data 87 on such a Y coordinate 99. The thus-obtained first package Y coordinate 107a corresponds to the second lead X coordinate 103b in the form of an integer. Conversely, searching is performed along the Y axis 99 vertically from bottom to top so as to find the Y coordinate 99 when the edge position flag 86 is "1". A second lead Y coordinate 105b is obtained by adding the above-mentioned Y coordinate 99 when the edge position flag is "1" to the edge position data 87 about such a Y coordinate 99. Searching is further performed to find the Y coordinate 99 when the edge position flag 86 is "F". A second Y coordinate 106b of the light-shielding band pattern is obtained by adding the above-mentioned Y coordinate 99 when the edge position flag 86 is "F" to the edge position data 87 about such a Y coordinate 99. Then, searching is performed vertically from bottom to top along the Y axis 99 with respect to the second package X coordinate 104b in the form of an integer. Through this searching, the Y coordinate 99 when the edge position flag 86 is "1" is found. A second package Y coordinate 107b is obtained by adding the above-mentioned Y coordinate 99 when the edge position flag 86 is "1" to the edge position data 87 about such a Y coordinate 99. The thus-obtained X and Y coordinates about all the leads 2 and the package 1a detected through the foregoing searching result in the detected position information 39.

An explanation will now be given of the distance measurement means 41. FIG. 21 is a diagram produced by overlaying the detected position information 39 obtained by the position detection means 37 with the image information 31 shown in FIG. 18. The first lead and light-shielding band pattern distance data 41a can be indicated by an absolute value indicative of a disparity between the first lead Y coordinate 105a and the corresponding first light-shielding band pattern Y coordinate 106a. On the other hand, the second lead and light-shielding band pattern distance data 41b can be indicated by an absolute value indicative of a disparity between the second lead Y coordinate 105b and the corresponding second light-shielding band pattern Y coordinate 106b. The first package and light-shielding band pattern distance data 41c can be indicated by an absolute value indicative of a disparity between the first package Y coordinate 107a and the corresponding first light-shielding band pattern Y coordinate 106a. On the other hand, the second package and light-shielding band pattern distance data 41d can be indicated by an absolute value indicative of a disparity between the second package Y coordinate 107b and the corresponding second light-shielding band pattern Y coordinate 106b. The first lead and package distance data 41e can be indicated by an absolute value indicative of a disparity between the first lead Y coordinate 105a and the corresponding first package Y coordinate 107a. On the other hand, the second lead and package distance data 41f can be indicated by an absolute value indicative of a disparity between the second lead Y coordinate 105b and the corresponding second package Y coordinate 107b.

The first lead and light-shielding band pattern distance information 42a results from the first lead and light-shielding band pattern distance data 41a indicative of all the leads 2 contained in the first optical information 23 which is used to produce the first and second image information items 31a and 31b. The second lead and light-shielding band pattern distance information 42b results from the second lead and light-shielding band pattern distance data 41b indicative of all the leads 2 contained in the second optical information 25 which is used to produce the first and second image information 31a and 31b. The first package and light-shielding band pattern distance information 44a results from the first package and light-shielding band pattern distance data 41c indicative of all the packages 1a contained in the first optical information 23 which is used to produce the first and second image information items 31a and 31b. The second package and light-shielding band pattern distance information 44b results from the second package and light-shielding band pattern distance data 41d indicative of all the packages 1a contained in the second optical information 25 which is used to produce the first and second image information items 31a and 31b. The first lead and package distance information 46a results from the first lead and package distance data 41e indicative of all the leads 2 contained in the first optical information 23 which is used to produce the first and second image information items 31a and 31b. The second lead and package distance information 46b results from the second lead and package distance data 41f indicative of all the leads 2 contained in the second optical information 25 which is used to produce the first and second image information items 31a and 31b.

Figure 22:
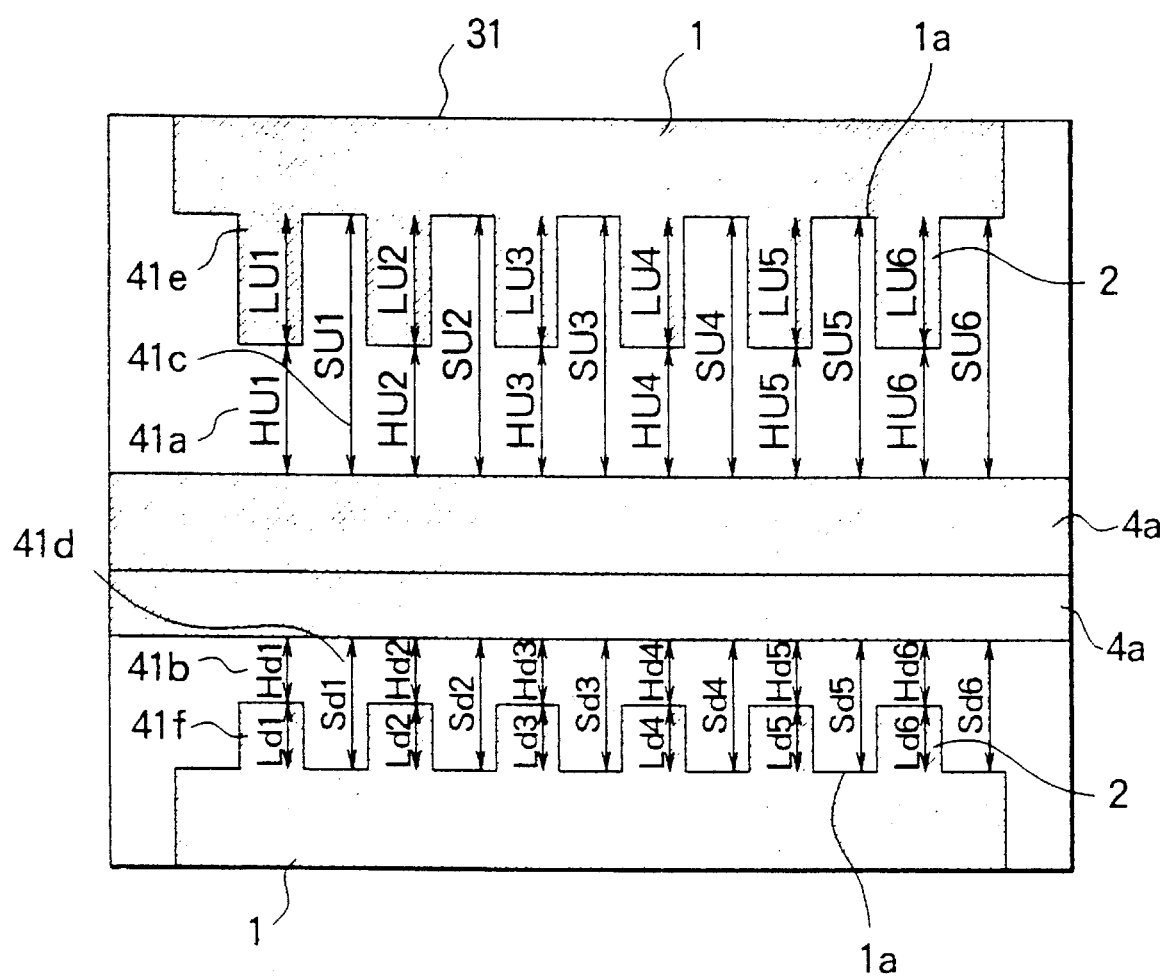
FIG. 22 a schematic diagram obtained by overlapping distance measurement information over the image information shown in FIG. 18.
Figure 23:
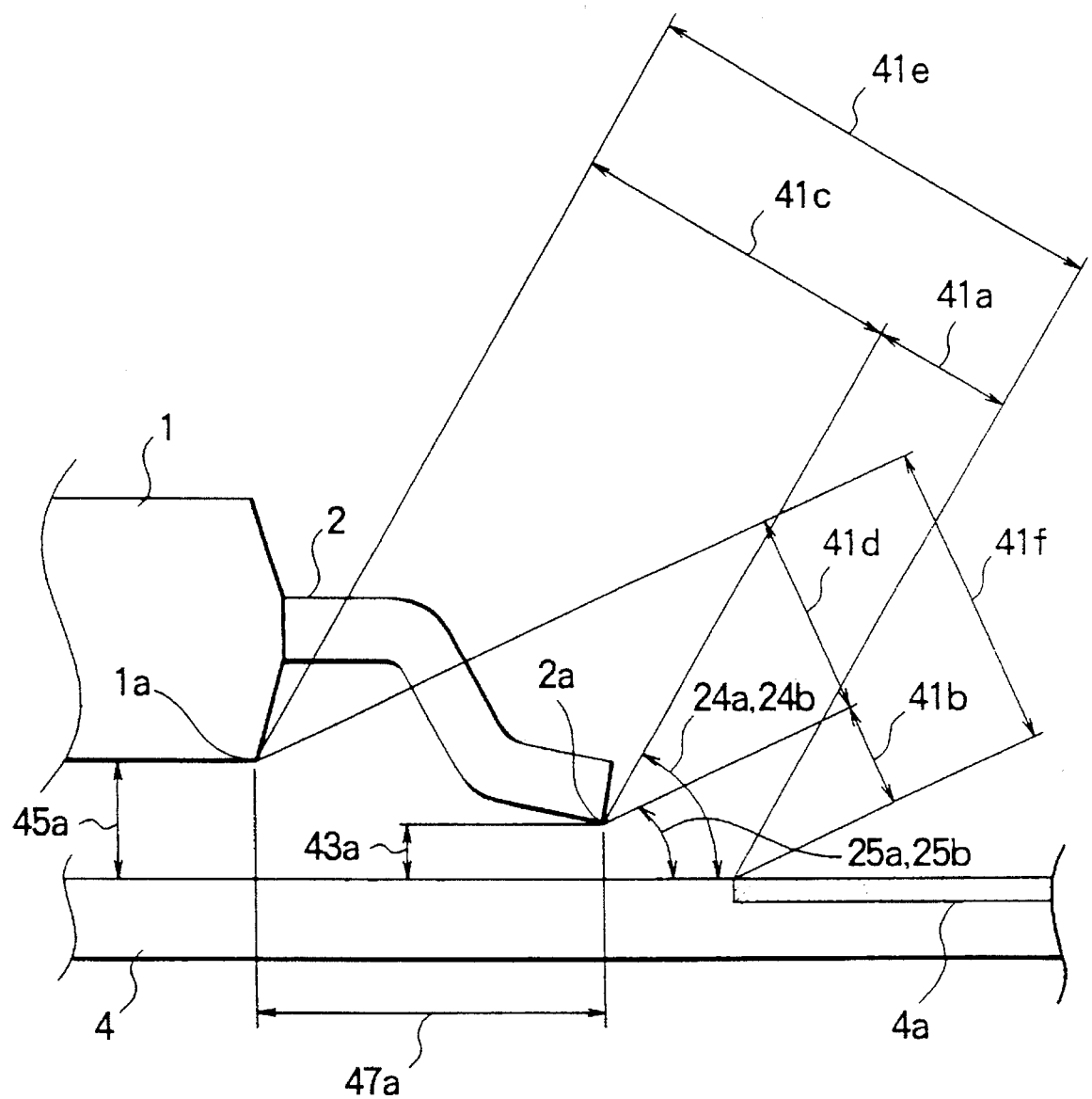
FIG. 23 is a partial side view of a semiconductor device on the transparent mounting plate.

A description will now be given of the flatness measurement means 43, the stand-off measurement means 45 and the lead length measurement means 47. FIG. 22 is a diagram produced by overlaying the respective distance information items described above obtained by the distance measurement means 41 with the image information 31 shown in FIG. 18. FIG. 23 is a partial side view of the semiconductor device 1 placed on the transparent mounting plate 4, as viewed in the horizontal direction.

The flatness measurement means 43 uses the first image information 31a to calculate the following equation 2 from the first lead and light-shielding band pattern distance data 41a obtained from the first image information 31a, the second lead and light-shielding band pattern distance data 41b, which lead is the same as the one of the data 41a, and the first and second angles of elevation 24a and 26a in the first optical section 22a, thereby producing the flatness data 43a indicative of the height from the transparent mounting plate 4 to the lead 2. The flatness measurement means 43 also uses the second image information 31b to calculate the following equation 2 from the first lead and light-shielding band pattern distance data 41a obtained from the second image information 31b, the second lead and light-shielding band pattern distance data 41b, which lead is the same as the one used in the data 41a, the first and second angles of elevation 24b and 26b in the second optical section 22b, thereby calculating the flatness data 43a indicative of the height from the transparent mounting plate 4 to the lead 2. In consequence, the flatness data 43a indicative of all the leads 2 of the semiconductor device 1 can be calculated, thereby determining the flatness measurement information 55. It should be noted that the first angles of elevation 24a and 24b will be hereinafter simplified as the first angle of elevation 24, and the second angles of elevation 26a and 26b will be hereinafter simplified as the second angle of elevation 26, as required.

Flatness data 43a = {(second lead and light-shielding band pattern distance data 41b * SIN(first angle of elevation 24)) − (first lead and light-shielding band pattern distance data 41a * SIN(second angle of elevation 26)} / {COS (second angle of elevation 26) * SIN(first angle of elevation 24) − COS(first angle of elevation 24) * SIN(second angle of elevation 26)}  Equation 2

The stand-off measurement means 45 employs the first image information 31a to calculate the following equation 3 from the first package and light-shielding band pattern distance data 41c obtained from the first image information 31a, the second package and light-shielding band pattern distance data 41d, which package is the same as the one of the data 41c, and the first and second angles of elevation 24a and 26a in the first optical section 22a, thereby calculating the stand-off characteristics data 45a. The stand-off measurement means 45 employs the second image information 31b to calculate the following equation 3 for the first package and light-shielding band pattern distance data 41c obtained from the second image information 31b, the second package and light-shielding band pattern distance data 41d, which package is the same as the of the data 41c, and the first and second angles of elevation 24b and 26b in the second optical section 22b, thereby calculating the stand-off characteristics data 45a. In consequence, the stand-off characteristics data 45a indicative of all the leads 2 of the semiconductor device 1 and the package 1a between the leads 2 can be calculated, thereby obtaining the stand-off measurement information 56.

Stand-off characteristics data 45a = {(second package and light-shielding band pattern distance data 41c * SIN(first angle of elevation 24) − (first package and light-shielding band pattern distance data 41d * SIN(second angle of elevation 26))} / {COS(second angle of elevation 26) * SIN(first angle of elevation 24) − COS(first angle of elevation 24) * SIN(second angle of elevation 26)}     Equation 3

The lead length measurement means 47 employs the first image information 31a to calculate the following equation 4 from the first lead and package distance data 41e obtained from the first image information 31a, the second lead and package distance data 41f, which lead is the same as the one of the data 41e, and the first and second angles of elevation 24a and 26a in the first optical section 22a, thereby calculating the lead length data 47a, which length is measured from the package 1a to the lead end 2a. The lead length measurement means 47 employs the second image information 31b to calculate the following equation 4 from the first lead and package distance data 41e obtained from the second image information 31b, the second lead and package distance data 41f, which lead is the same as the one of the data 41e, and the first and second angles of elevation 24b and 26b in the second optical section 22b, thereby calculating the lead length data 47a, which length is measured from the package 1a to the lead end 2a. In consequence, the lead length data 47a indicative of all the leads 2 of the semiconductor device 1 can be calculated, thereby obtaining the lead length measurement information 57.

Lead length data 47a = { second lead and package distance data 41f * COS (first angle of elevation 24) − (first lead and package distance data 41e * COS (second angle of elevation26))} / {SIN (second angle of elevation 26) * COS (first angle of elevation 24) − SIN (first angle of elevation 24) * COS (second angle of elevation 26)}     Equation 4

Figure 24:
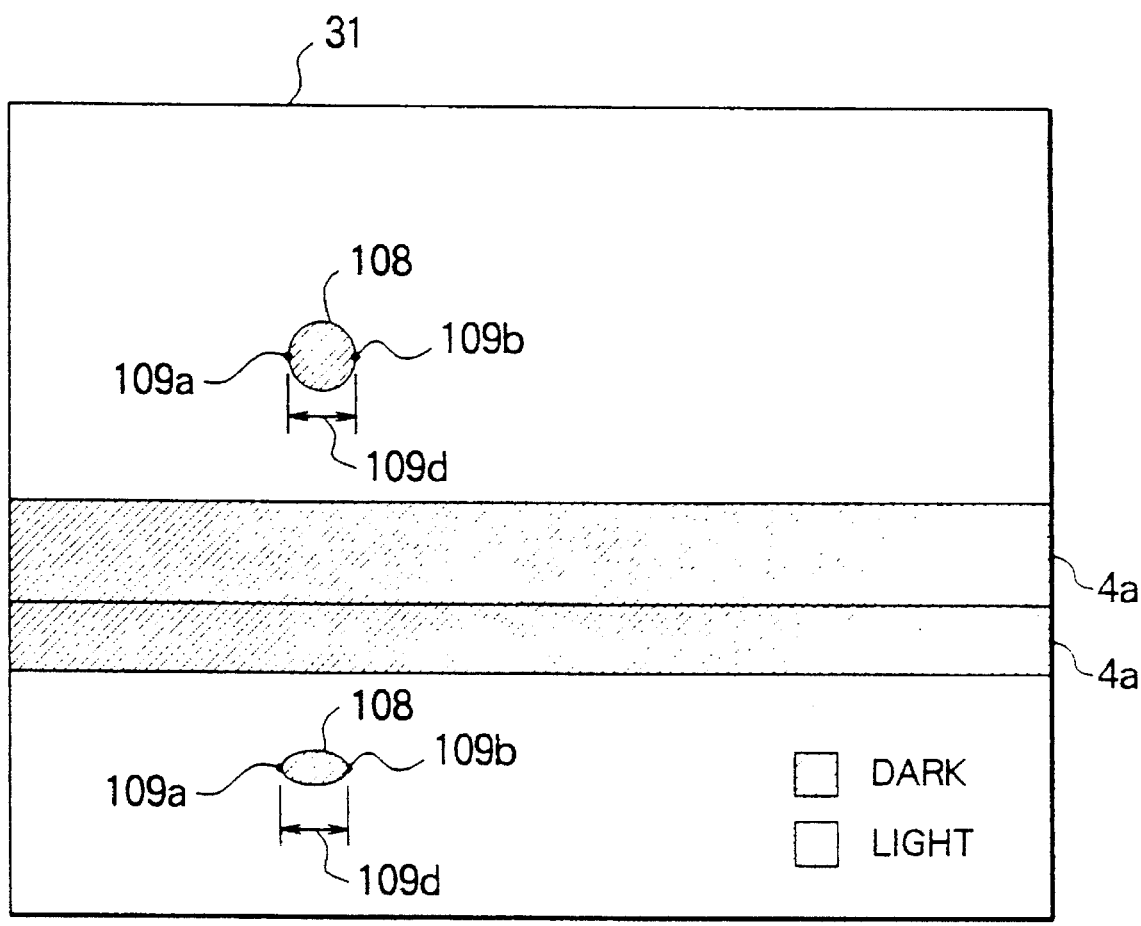
FIG. 24 is a schematic view of one example of the image information obtained when there is no semiconductor device mounted on the transparent mounting plate.

An explanation will now be given of the abnormality detection means 40. FIG. 24 illustrates one example of the image information 31 which has been obtained when there was no semiconductor device 1 on the transparent mounting plate 4. Only one abnormal item (extraneous matter) 108 is shown in FIG. 24. When the position detection means 37 detects the abnormal matter 108 causing a change of brightness which should be normally caused only by the light-shielding band pattern 4a, it outputs an abnormal-matter left-hand X coordinate 109a and an abnormal-matter right-hand X coordinate 109b as the abnormality information 39. When the abnormality detection means 40 detects the abnormal-matter left-hand X coordinate 109a, it forms the abnormality information 38 indicating the number of abnormal-matter left-hand X coordinates 109a and pairs of the abnormal-matter left-hand and right-hand X coordinates 109a and 109b so as to detect the number 109c of abnormal matters 108. The abnormality detection means 40 subtracts the abnormal-items left-hand X coordinate 109a from the abnormal-matter right-hand X coordinate 109b so as to measure the dimensions 109d of the abnormal matter 108. In contrast, when the abnormal-matter left-hand and right-hand X coordinates 109a and 109b are not detectable, the number 109c of the abnormal items is set to "0", and the results in the first and second image information items 31a and 31b are totaled so that the detected abnormality information 54 is output.

Figure 25:
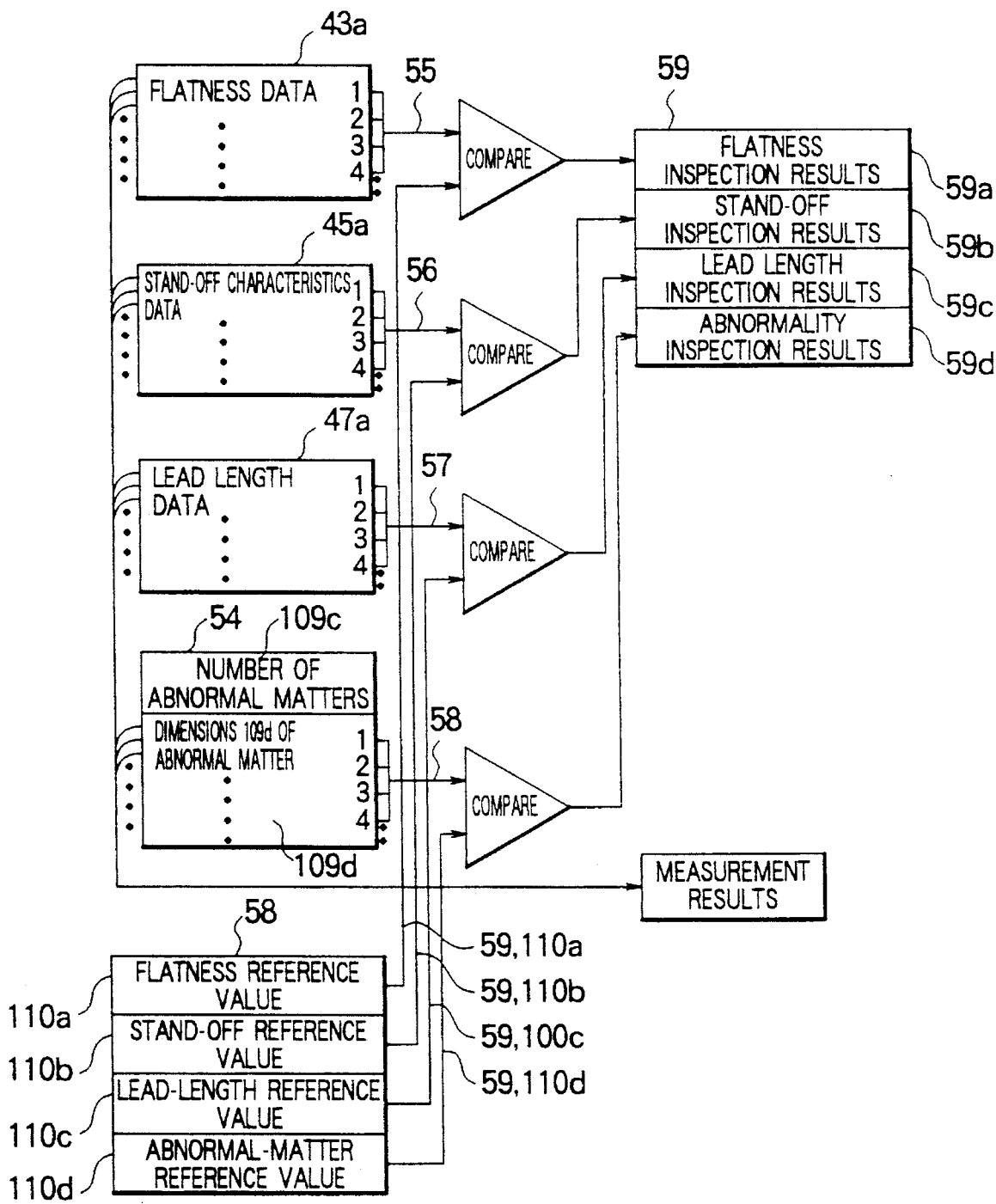
FIG. 25 is a block diagram illustrative of the operation of inspection means.

The inspection means 53 will now be explained. FIG. 25 is a block diagram illustrative of one example of the inspection means 53. The inspection means 53 compares a group of flatness data 43a resulting in the flatness measurement information 55 with a flatness reference value 110a which has already been registered in the type-of-semiconductor data 58. If all the flatness measurement information items 55 fall within the flatness reference value 110a, the inspection means 53 determines the flatness inspection results 59a to be good. If not, the inspection means 53 determines the flatness inspection results 59a to be defective. Moreover, the inspection means 53 compares a group of the stand-off characteristic data 45a resulting in the stand-off measurement information 56 with a stand-off reference value 110b. If all the stand-off characteristic data items 45a fall within the stand-off reference value 110b, the inspection means 53 determines the stand-off inspection results 59b to be good. It not, the inspection means 53 determines the stand-off measurement results 59b to be defective. Further, the inspection means 53 compares a group of the lead length data 47a resulting in the lead length measurement information 57 with a lead length reference value 110c. If all the lead length data items 47a fall within the lead length reference value 110c, the inspection means 53 determines the lead length inspection results 59c to be good. It not, the inspection means 53 determines the lead length measurement results 59c to be defective. Still further, the inspection means 53 determines abnormality inspection results 59d to be good when the number 109c of the abnormal items 108 obtained from the detected abnormality information 54 is "0". Even though it is not "0" and if all the dimensions 109d of the abnormal items 108 fall within the abnormal-matter reference value 110d, the inspection means 53 determines that such an abnormal matter 108 has no adverse influence on the measurement of the semiconductor device 1 and can thus be safely ignored. If the number 109c of the abnormal items 108 is not "0" and if the dimensions 109d of the abnormal items 108 exceed the abnormal-matter reference value 110d, the inspection means 53 determines the abnormality inspection results 59d to be defective. The inspection means 53 outputs such inspection results 59 to the feeding control section 62 and also outputs the inspection results 59 and the measurement information 60 to the display means 61.

If all the inspection results 59 are good, the feeding control section 62 feeds a semiconductor device 1 to a non-defective goods storage section (not shown). If the inspection results 59 contain a defective item, the feeding control section 62 feeds such a semiconductor device 1 to a defective goods storage section (not shown). If the overall abnormality inspection results 59 are defective, the feeding control section 62 interrupts the feeding operation and gives a warning (not shown) indicating that an abnormality has occurred on the transparent mounting plate 4.

Figure 26:
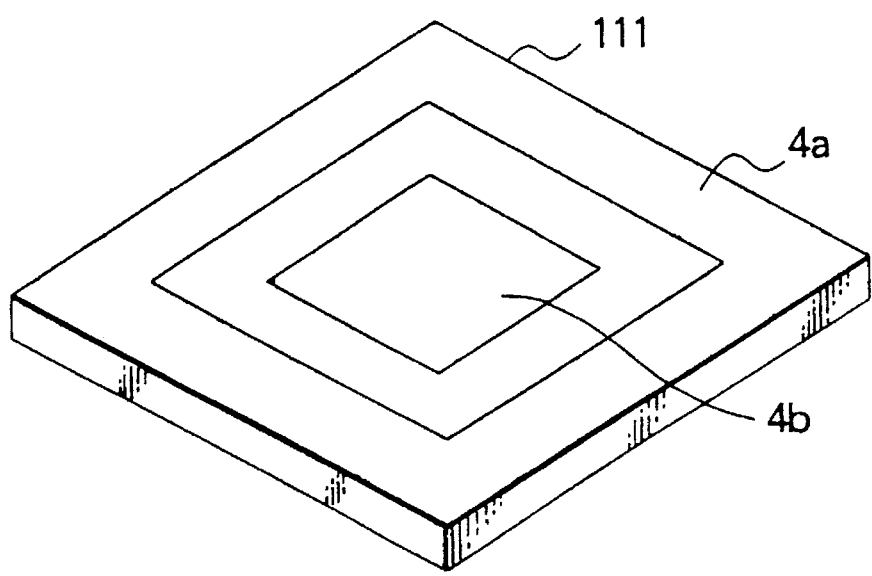
FIG. 26 is a perspective view illustrative of one example of a transparent mounting plate for measuring the angle of elevation.
Figure 27:
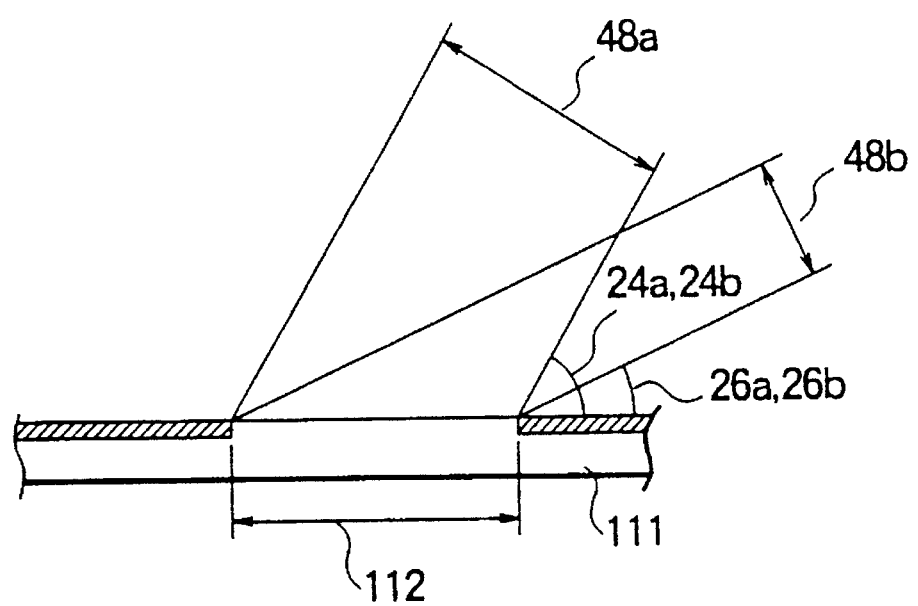
FIG. 27 is a partial side view of the angle-of-elevation measurement transparent mounting plate.
Figure 28:
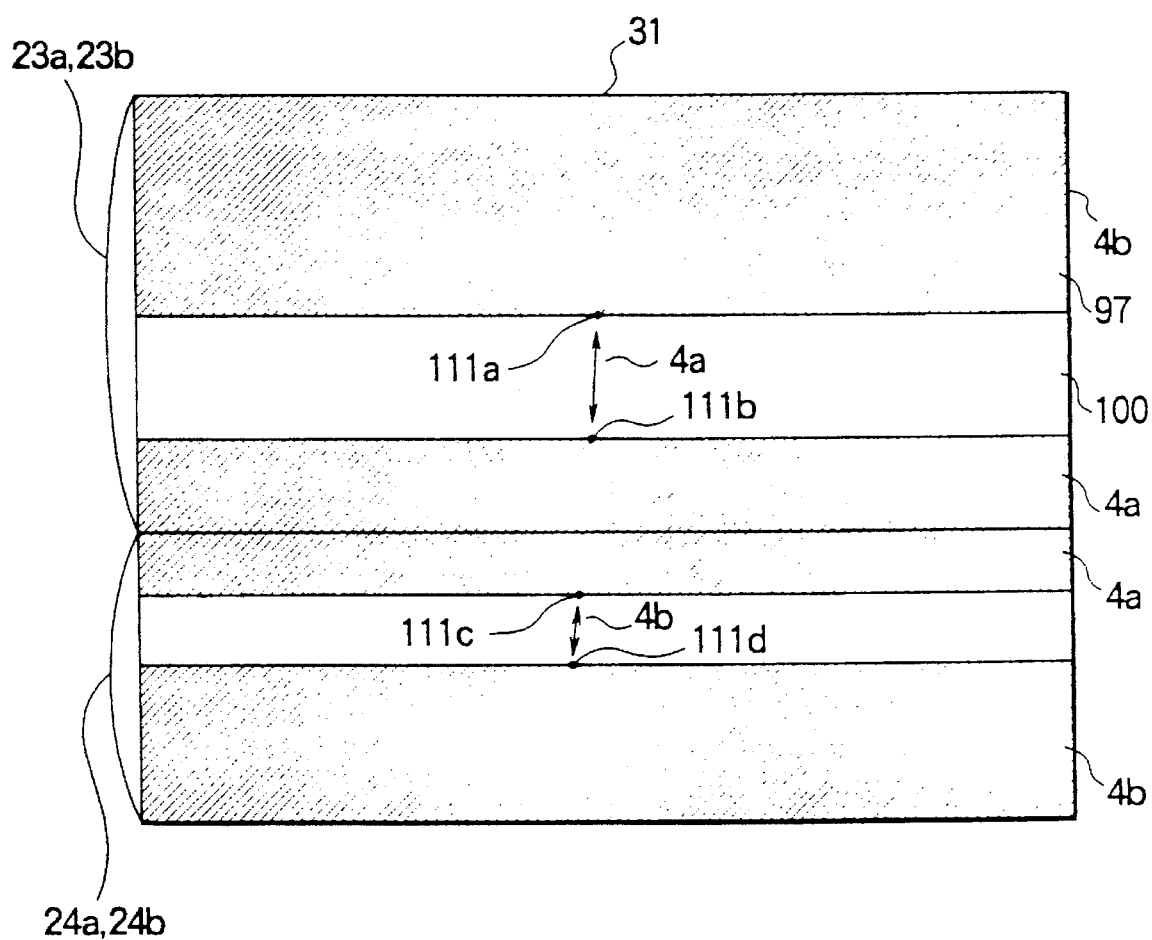
FIG. 28 is a schematic view of one example of image information of the angle-of-elevation measurement transparent mounting plate.

A description will now be given of the angle-of-elevation measurement means 49. FIG. 26 is a perspective view of a transparent mounting plate 111 for measuring the angle of elevation. A light-shielding band pattern 4a, and a light-shielding pattern 4b which is placed across and a predetermined distance from the band pattern 4a are formed on the transparent mounting plate 4. FIG. 27 is a side view of the angle-of-elevation measurement transparent mounting plate 111, as viewed in the horizontal direction. FIG. 28 illustrates one example of the image information 31 from the transparent mounting plate 111. When it is not necessary to measure the dimensions of the semiconductor device 1, the transparent mounting plate 4 is removed from the mounting base 3, and instead, the angle-of-elevation measurement transparent mounting plate 111 is placed thereon.

Subsequently, the image information 31 is stored in the image input storage means 32. The position detection means 37 searches the optical information 23 vertically from top to bottom for the position of the light-shielding pattern 4b. The position detection means 37 then averages all the positions of the light-shielding pattern 4b in which the brightness changes from the dark portion 97 to the light portion 100 so as to determine an averaged value as first light-shielding pattern position data 111a. The position detection means 37 also averages all the positions of the light-shielding band pattern 4a in which the brightness changes from the light portion 100 to the dark portion 97 so as to determine the averaged value as first light-shielding band pattern position data 111b. On the other hand, the position detection means 37 searches the second optical information 25 vertically from top to bottom for the position of the light-shielding band pattern 4a. The position detection means 37 then averages all the positions of the light-shielding band pattern 4a in which the brightness changes from the dark portion 97 to the light portion 100 so as to determine the averaged value as second light-shielding band pattern position data 111c. The position detection means 37 also averages all the positions of the light-shielding pattern 4b in which the brightness changes from the light portion 100 to the dark portion 97 so as to determine the averaged value as second light-shielding pattern position data 111d. The thus-obtained position information 39 is output.

The distance measurement means 41 outputs the first light-shielding pattern distance information 48a which is an absolute value indicative of a disparity between the first light-shielding pattern position data 111a and the first light-shielding band pattern position data 111b. The distance measurement means 41 also outputs the second light-shielding pattern distance information 48b which is an absolute value indicative of a disparity between the second light-shielding pattern position data 111d and the second light-shielding band pattern position data 111c.

The angle-of-elevation measurement means 49 calculates the first angle of elevation 24 according to the following equation 5 using the first light-shielding pattern distance information 48a and known light-shielding pattern dimensions 112. The angle-of-elevation measurement means 49 also calculates the second angle of elevation 26 according to the following equation 6 using the second light-shielding pattern distance information 48b and the known light-shielding pattern dimensions 112.

The first and second angles of elevation 24a and 26a in the first optical section 22a are measured by means of the first image information, i.e., light ray 31a, while the first and second angles of elevation 24b and 26b in the second optical section 22b are measured by means of the second image information, i.e., light ray 31b. The thus-obtained angles of elevation items are stored in the angle-of-elevation data 51.

First angle-of-elevation data 24 = ARCSIN (first light-shielding pattern distance information 48a/light-shielding pattern dimensions 112)  Equation 5

Second angle-of-elevation data 26 = ARCSIN (second light-shielding pattern distance information 48b/light-shielding pattern dimensions 112)  Equation 6

Figure 29:
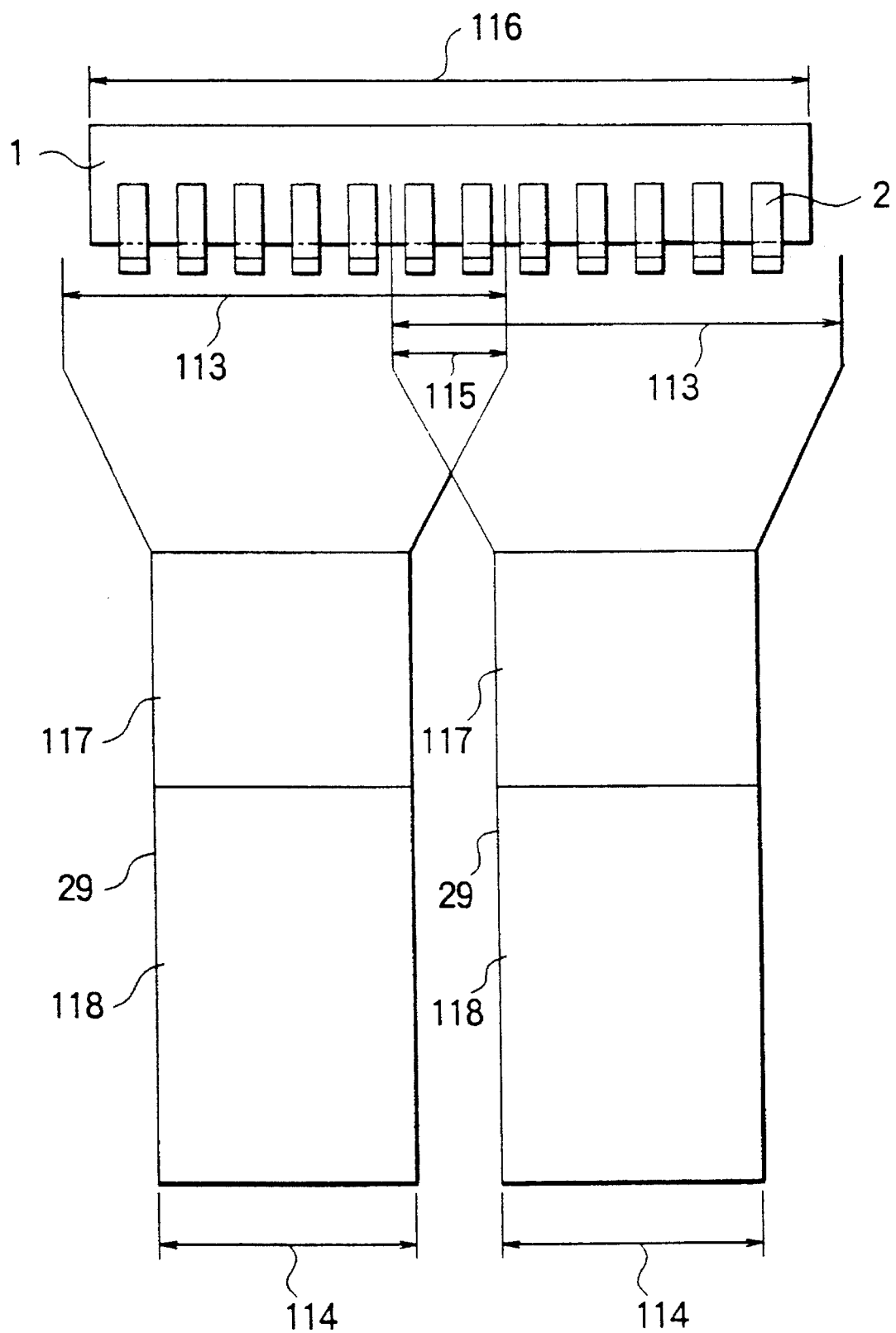
FIG. 29 illustrates one example of a plurality of imaging devices arranged side by side when a dimension of a semiconductor device is greater than that of a field of view of the imaging device.

FIG. 29 illustrates one example of a plurality of imaging devices 29 arranged side by side when a dimension of the semiconductor device 1 is greater than that of a field of view 113 of the image information 31. FIG. 29 is a side view of the semiconductor device 1 and a plurality of imaging devices 29, as horizontally viewed from the lead axis. The optical information reflecting means, the transparent mounting plate 4, and other components, are not shown. The plurality of imaging devices 29 are arranged so that the dimension 114 of each of the imaging devices 29 is smaller than that of the field of view 113 of the image information 31, and one field of view 113 is overlapped with another field of view 113, the overlapped portion being indicated by reference numeral 115. Thus, the plurality of imaging devices 29 are arranged parallel to the lateral surface of the semiconductor device 1 so that the overall field of view 113 can cover the dimension of one lateral surface of the semiconductor device 1. The relationship between the dimension of the semiconductor device 1 and other factors can be indicated by the following expression 7. The imaging device 29 comprises a lens section 117 and an imaging section 118.

Dimension 116 of semiconductor device < dimension of field of view 113 * number of imaging devices − overlapped dimension 115 * (number of imaging devices - 1) > dimension 114 of imaging devices * number of imaging device  Expression 7

Second Embodiment

Figure 30:
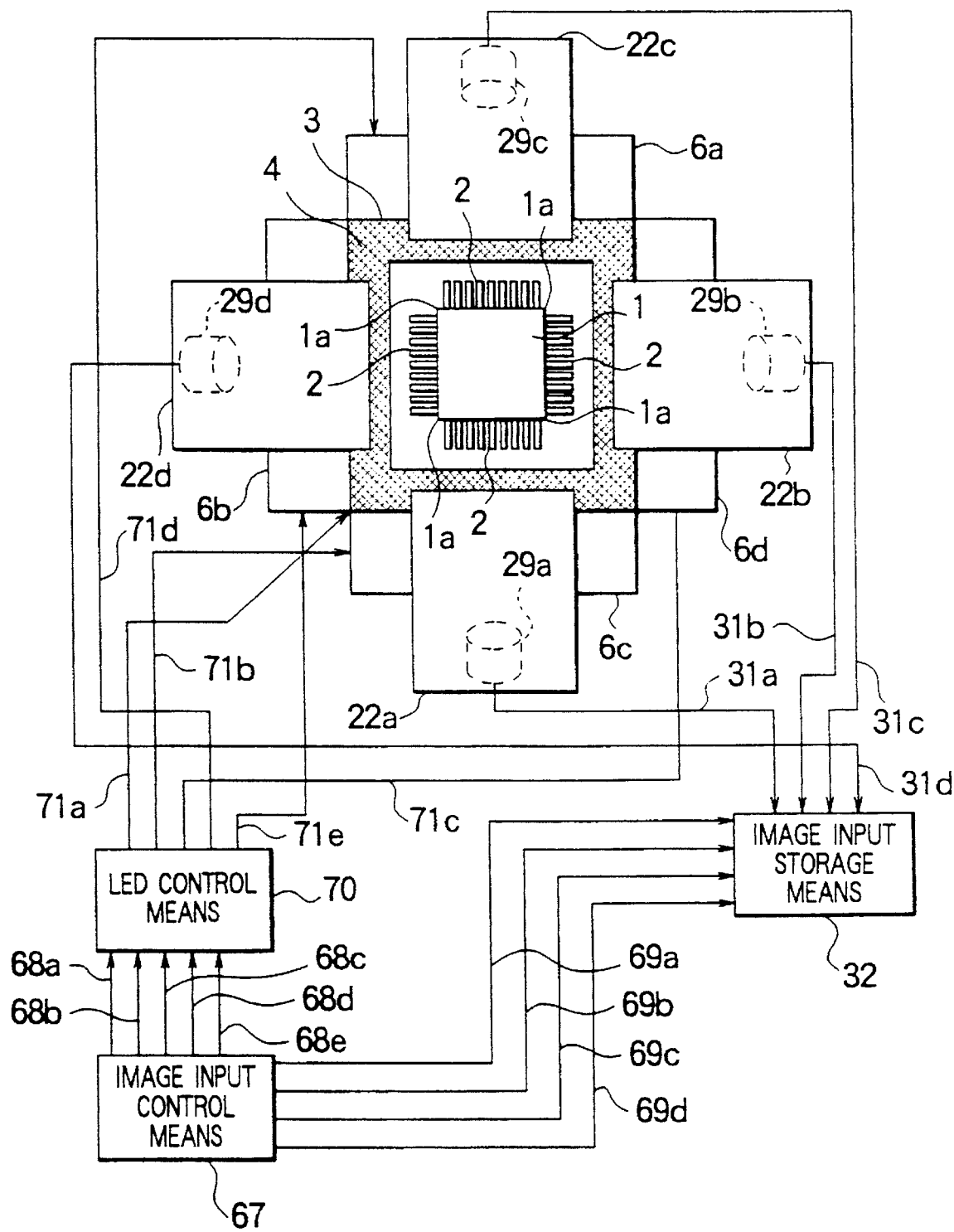
FIG. 30 is a schematic view of the construction of a semiconductor-device measurement apparatus according to a second embodiment of the present invention.

FIG. 30 is a schematic top view illustrative of a semiconductor-device measurement apparatus according to a second embodiment of the present invention. FIG. 30 schematically shows: a mounting base 3; a transparent mounting plate 4 having the semiconductor device 1 mounted thereon; first, second, third and fourth optical sections 22a–22d; LED control means 70; image input storage means 32; and the image input control means 67. The other components are similar to those shown in FIG. 1, and an explanation thereof will thus be omitted. FIG. 30 also shows: third and fourth optical sections 22c and 22d; third and fourth imaging devices 29c and 29d; third and fourth LED illumination units 6c and 6d; third and fourth LED luminous signals 68c and 68d, respectively, which are output from the image input control means 67 and input to the LED control means 70; third and fourth LED luminous signals 71c and 71d which are controlled by the image input control means 67 and output from the LED control means 70; third image information, i.e., light ray, 31c which is output from the third imaging device 29c and input to the image input storage means 32; fourth image information, i.e., light ray, 31d which is output from the fourth imaging device 29d and input into the image input storage means 32; and third and fourth image information input signals 69c and 69d which are output from the image input control means 67 and input into the image input storage means 32.

Figure 31:
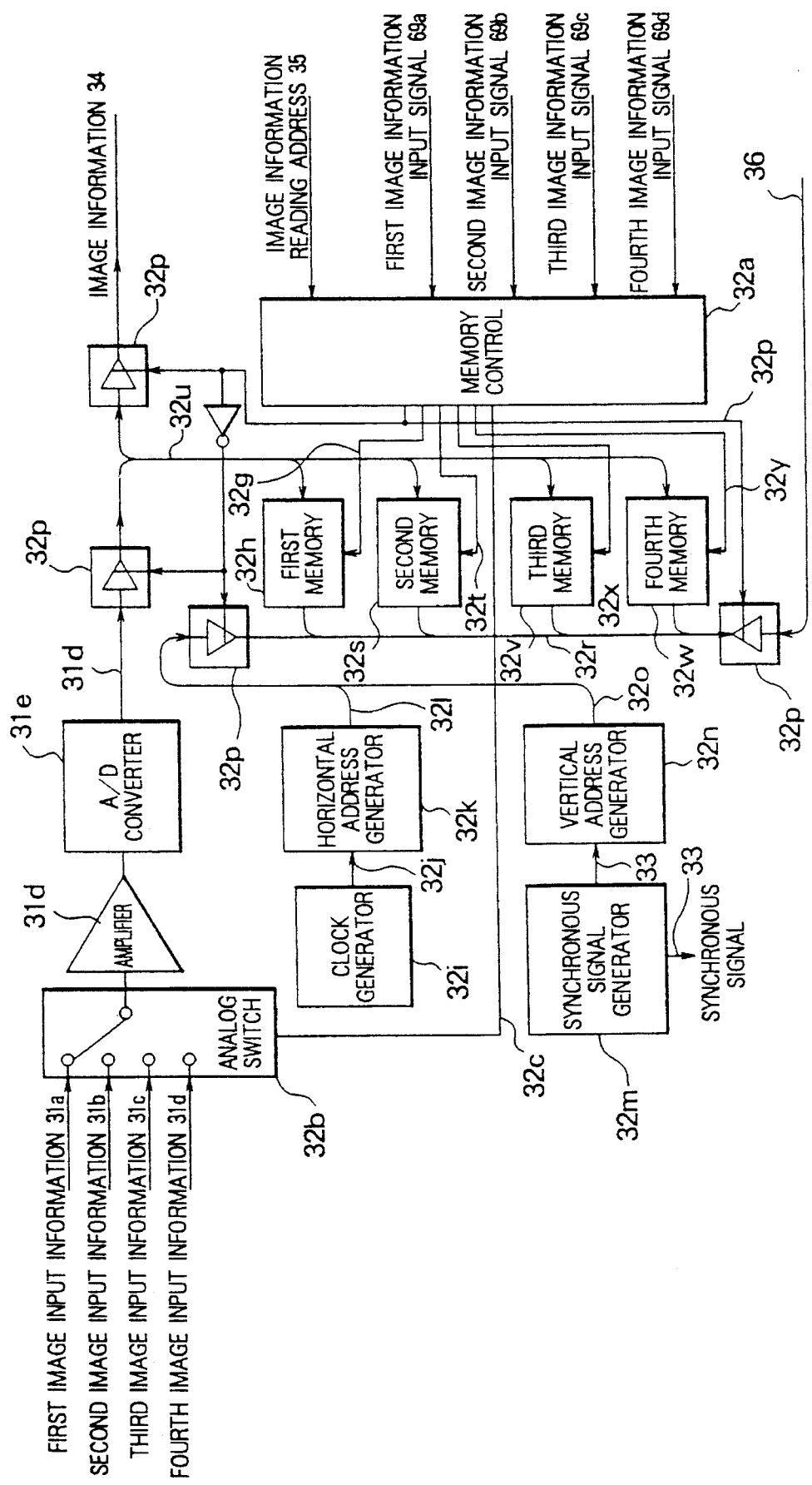
FIG. 31 is a block diagram illustrative of image input storage means according to the second embodiment of the present invention.

FIG. 31 illustrates another embodiment of the image input storage means 32. FIG. 31 shows a third memory 32v for receiving the third image information 31c, a fourth memory 32w for receiving the fourth image information 31d, a third control signal 32x for controlling the third memory 32v, and a fourth control signal 32y for controlling the fourth memory 32w.

As illustrated in FIG. 30, for the measurements of the dimensions of the semiconductor device 1 provided with leads 2 on four lateral surfaces of the package 1a, the semiconductor-device measurement apparatus is constructed as follows. An optical section is arranged on each of four lateral surfaces having the leads 2 mounted thereon. The four LED illumination units are each placed so as to correspond to each of the optical sections and are controlled by the LED control signals. The input of the respective image information items are controlled by the corresponding image information input signals, and the image information items are stored to the respective memories of the image input storage means.

Third Embodiment

Figure 32:
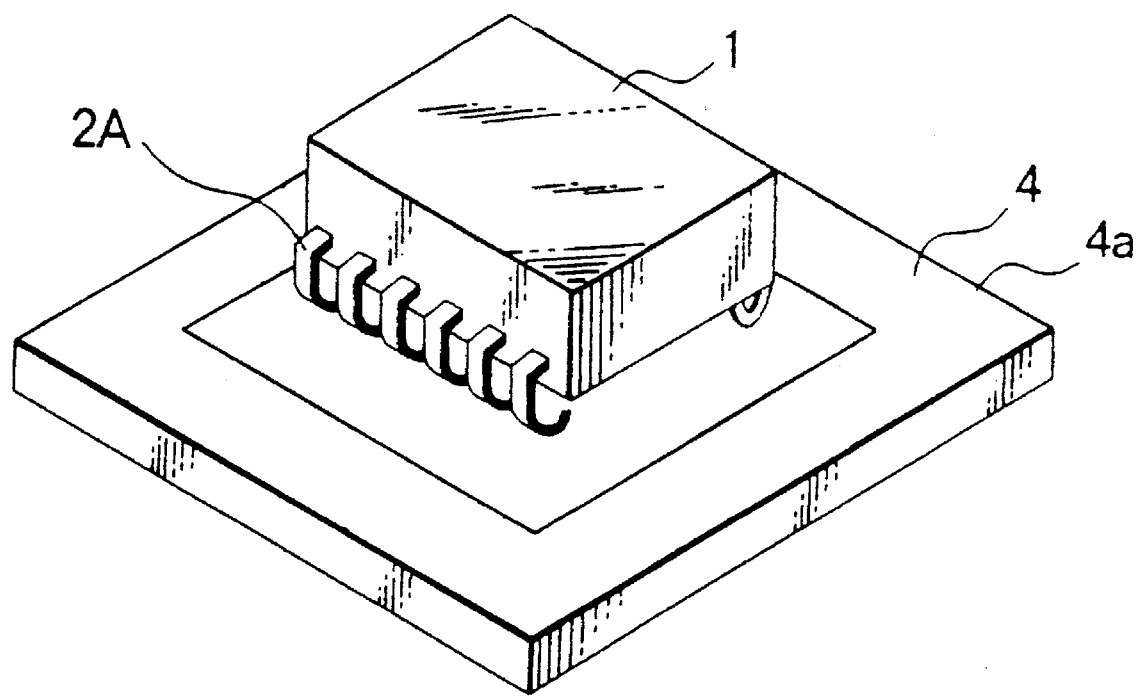
FIG. 32 is a perspective view illustrative of a semiconductor device having leads which are bent in a J-shape, the device being located on a transparent mounting plate.

FIG. 32 illustrates a semiconductor device 1 having J-shaped leads 2A, the device 1 being placed on the transparent mounting plate 4. According to this embodiment, measurements can also be performed on the semiconductor device 1 of the type which the leads 2A shown in FIG. 32 bend inward in the J-shape of the semiconductor device 1, in a manner similar to the measurements achieved in the foregoing embodiments.

What is claimed is:

1. A measurement apparatus for measuring dimensions of a semiconductor device comprising:

a transparent mounting plate for receiving a semiconductor device and having a light-shielding band pattern;

an illumination unit located on an opposite side of said transparent mounting plate from the semiconductor device;

first and second imaging devices for forming respective images from respective received first and second optical information light rays, the first and second optical information light rays being formed by light from said illumination unit passing tangent to lateral surfaces of the semiconductor device disposed on said transparent mounting plate, to said light-shielding band pattern and to leads projecting from the lateral surface, each first optical information light ray forming a first angle of elevation with said transparent mounting plate and each second optical information light ray forming a second angle of elevation with said transparent mounting plate, the first angle of elevation being larger than the second angle of elevation;

first and second optical information reflecting means for reflecting a first and a second optical information light ray, respectively, toward said first imaging device and third and fourth optical reflecting means for reflecting a first and a second optical information light ray, respectively, toward said second imaging device; and first equi-distance optical reflecting means located between said second optical information reflecting means and said first imaging device, and second equi-distance optical reflecting means located between said fourth optical information reflecting means and said second imaging device, said first equi-distance reflecting means reflecting one of the second optical information light rays from said second optical information reflecting means towards said first imaging device, and said second equi-distance reflecting means reflecting one of the second optical information light rays from the said fourth optical information reflecting means towards said second imaging device so that distances traveled by the first and second optical information light rays to a respective imaging device are equal.

2. The device according to claim 1 comprising:

storage means for storing images produced by said first and second imaging devices;

position detection means for detecting positions of the semiconductor device mounted on said transparent mounting plate and said light-shielding band pattern on said transparent mounting plate according to the images; and distance measurement means for measuring a distance between the semiconductor device mounted on said transparent mounting plate and said light-shielding band pattern.

3. The device according to claim 2, comprising:

a transparent mounting plate having an angle-of-elevation measurement pattern; and angle-of-elevation measurement means for measuring angles of elevation of the first and second optical information light rays output from said illumination unit.

4. The device according to claim 3 comprising flatness measurement means for measuring a height from said transparent mounting plate to each of the leads of the semiconductor device mounted on the transparent mounting plate according to distance information obtained by said distance measurement means and angle-of-elevation information obtained by said angle-of-elevation measurement means.

5. The device according to claim 3 comprising stand-off measurement means for measuring a height from said transparent mounting plate to a package of the semiconductor device mounted on said transparent mounting plate according to distance information obtained by said distance measurement means and angle-of-elevation information obtained by said angle-of-elevation measurement means.

6. A device according to claim 3, comprising lead length measurement means for measuring a length of each of the leads of the semiconductor device according to distance information obtained by said distance measurement means and angle-of-elevation information obtained by said angle-of-elevation measurement means.

7. The device according to claim 3 comprising abnormality detection means for detecting an abnormality of said transparent mounting plate when no semiconductor device is located on said plate according to abnormality information obtained by said position detection means.

8. The device according to claim 3 comprising:

abnormality detection means for detecting an abnormality of said transparent mounting plate when no semiconductor device is located on said plate;

flatness measurement means for measuring a height from said transparent mounting plate to each of the leads of the semiconductor device mounted on said transparent mounting plate;

stand-off measurement means for measuring a height from said transparent plate to the package of the semiconductor device mounted on said transparent mounting plate;

lead length measurement means for measuring a height from said transparent plate to the leads of the semiconductor device mounted on said transparent mounting plate; and inspection means for inspecting a detected abnormality obtained by said abnormality detection means, flatness obtained by said flatness measurement means, stand-off obtained by said stand-off measurement means, and lead length obtained by said lead length measurement means by comparison with respective predetermined reference values.

9. The device according to claim 2 wherein a light source of said illumination unit is an LED, said device comprising:

LED control means for controlling illumination output; and image input control means for controlling timing of input of the images into said storage means in cooperation with light emission from said LED.

10. The device according to claim 1, comprising a plurality of imaging devices each having a dimension of a field of view of image information smaller than that of the semiconductor device.

11. The device according to claim 1, comprising automatic feeding means for mounting the semiconductor device on said transparent mounting plate and removing it therefrom.

12. A method of measuring the dimensions of a semiconductor device comprising:

applying light in two different directions to a group of leads extending from a lateral surface of a semiconductor device and to a light-shielding band pattern on a transparent mounting plate supporting the semiconductor device;

forming two pairs of optical information light rays, each pair having different directions from the light applied in two different directions that is tangent to the leads of the semiconductor device and the light-shielding band pattern;

forming respective images from each pair of optical information light rays;

storing the respective images;

detecting a position of a forward end of each of the leads extending from a lateral surface of the semiconductor device and a position of the light-shielding band pattern relative to each of the leads using a pair of the optical information light rays;

measuring a distance from the forward end of each of the leads to the light-shielding band pattern corresponding to each of the leads using a pair of the optical information light rays and to produce distance information;

measuring flatness of each of the leads from the distance information and from angles of elevation of two optical information light rays with the transparent mounting plate; and sequentially measuring the flatness of the leads for each of the lateral surfaces from which leads extend, thereby measuring a height of each of the leads of the semiconductor device from the transparent mounting plate.

13. The method according to claim 12 including detecting the position of the light-shielding band pattern from a variance in brightness of the images with a resolution smaller than one pixel.

* * * * *